(12) United States Patent
Tsopanoglou et al.

(10) Patent No.: US 8,389,476 B2
(45) Date of Patent: Mar. 5, 2013

(54) PARSTATIN PEPTIDES AND USES THEREOF

(75) Inventors: Nikos E. Tsopanoglou, Achala (GR);
Michael E. Maragoudakis, Attiki (GR);
Stan Vinores, Baltimore, MD (US);
Sotirios Gartaganis, Rio-Patras (GR);
Jennifer L. Strande, Milwaukee, WI (US)

(73) Assignees: The Johns Hopkins University School of Medicine, Baltimore, MD (US);
Medical College of Wisconsin, Milwaukee, WI (US)

( * ) Notice: Subject to any disclaimer, the term of this patent is extended or adjusted under 35 U.S.C. 154(b) by 415 days.

(21) Appl. No.: 12/645,991

(22) Filed: Dec. 23, 2009

(65) Prior Publication Data

US 2010/0197580 A1  Aug. 5, 2010

Related U.S. Application Data

(63) Continuation-in-part of application No. 12/572,018, filed on Oct. 1, 2009, now abandoned, which is a continuation-in-part of application No. 12/054,712, filed on Mar. 25, 2008.

(60) Provisional application No. 60/908,707, filed on Mar. 29, 2007.

(51) Int. Cl.
*A61K 38/16* (2006.01)
(52) U.S. Cl. ............... 514/13.3; 514/16.4; 514/20.8; 514/21.3
(58) Field of Classification Search .................. None
See application file for complete search history.

(56) References Cited

FOREIGN PATENT DOCUMENTS
WO  WO 98/16548  *  4/1998

* cited by examiner

*Primary Examiner* — Christina Bradley
(74) *Attorney, Agent, or Firm* — Edwards Wildman Palmer LLP; Peter F. Corless; Richard B. Emmons

(57) ABSTRACT

The invention provides parstatin peptides, particularly a mammalian parstatin peptide including amino acids 1-26 of full length mammalian parstatin, preferably a human parstatin. The invention provides parstatin peptides in appropriate pharmaceutical carriers and formulated for administration. The invention provides for the use of the peptide for example as a medicament or for the preparation of a medicament. The invention provides methods of use for parstatin peptides including for inhibition of angiogenesis, for example for inhibition of ocular angiogenesis, for methods of cardioprotection, and for methods of prevention and treatment of myocardial ischemia-reperfusion injury.

16 Claims, 10 Drawing Sheets

E

Control (PBS)     Parstatin 2 x 75µg     Parstatin 2 x 100µg

D

Chemical-burned induced corneal neovascularization after parstatin treatment

E

A

B

A

B

C

SEQUENCE LISTING

```
<160> NUMBER OF SEQ ID NOS: 8

<210> SEQ ID NO 1
<211> LENGTH: 41
<212> TYPE: PRT
<213> ORGANISM: homo sapien

<400> SEQUENCE: 1

Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg
        35                  40

<210> SEQ ID NO 2
<211> LENGTH: 41
<212> TYPE: PRT
<213> ORGANISM: artificial sequence
<220> FEATURE:
<223> OTHER INFORMATION: Synthetic peptide

<400> SEQUENCE: 2

Leu Arg Thr Asn Ala Ser Leu Leu Val Pro Phe Leu Thr Ala Arg Ala
1               5                   10                  15

Lys Ser Ser Gly Thr Arg Glu Ala Ala Asp Pro Pro Arg Leu Met Cys
            20                  25                  30

Leu Arg Pro Leu Ala Arg Arg Cys Gly
        35                  40

<210> SEQ ID NO 3
<211> LENGTH: 41
<212> TYPE: PRT
<213> ORGANISM: Cricetulus longicaudatus

<400> SEQUENCE: 3

Met Gly Pro Gln Arg Leu Leu Leu Val Ala Ala Gly Leu Ser Leu Cys
1               5                   10                  15

Gly Pro Leu Leu Ser Ser Arg Val Pro Val Arg Gln Pro Glu Ser Glu
            20                  25                  30

Met Thr Asp Ala Thr Val Asn Pro Arg
        35                  40
```

```
<210> SEQ ID NO 4
<211> LENGTH: 41
<212> TYPE: PRT
<213> ORGANISM: mus musculus

<400> SEQUENCE: 4

Met Gly Pro Arg Arg Leu Leu Ile Val Ala Leu Gly Leu Ser Leu Cys
 1               5                  10                  15

Gly Pro Leu Leu Ser Ser Arg Val Pro Met Ser Gln Pro Glu Ser Glu
            20                  25                  30

Arg Thr Asp Ala Thr Val Asn Pro Arg
        35                  40

<210> SEQ ID NO 5
<211> LENGTH: 41
<212> TYPE: PRT
<213> ORGANISM: Macaca mulatta

<400> SEQUENCE: 5

Met Gly Pro Arg Arg Leu Leu Val Ala Ala Cys Leu Cys Leu Cys
 1               5                  10                  15

Gly Pro Leu Leu Ser Ala Arg Thr Arg Ala Arg Arg Pro Ala Ser Lys
            20                  25                  30

Ala Thr Asn Ala Thr Leu Asp Pro Arg
        35                  40

<210> SEQ ID NO 6
<211> LENGTH: 41
<212> TYPE: PRT
<213> ORGANISM: Rattus norvegicus

<400> SEQUENCE: 6

Met Gly Pro Arg Arg Leu Leu Val Ala Val Gly Leu Ser Leu Cys
 1               5                  10                  15

Gly Pro Leu Leu Ser Ser Arg Val Pro Met Arg Gln Pro Glu Ser Glu
            20                  25                  30

Arg Met Tyr Ala Thr Pro Tyr Ala Thr
        35                  40

<210> SEQ ID NO 7
<211> LENGTH: 41
<212> TYPE: PRT
<213> ORGANISM: Bos taurus

<400> SEQUENCE: 7

Met Gly Pro Arg Trp Leu Leu Trp Ala Ala Gly Leu Gly Leu Cys
 1               5                  10                  15

Ser Pro Leu Val Ser Ala Arg Thr Arg Gly Pro Arg Pro Gly Thr Asp
            20                  25                  30

Pro Thr Asn Gly Thr Leu Gly Pro Arg
        35                  40

<210> SEQ ID NO 8
<211> LENGTH: 6
<212> TYPE: PRT
<213> ORGANISM: homo sapien

<400> SEQUENCE: 8

Ser Phe Leu Leu Arg Asn
 1               5
```

PARSTATIN PEPTIDES AND USES THEREOF

CROSS-REFERENCE TO RELATED APPLICATIONS

This application is a continuation-in-part application that claims priority to U.S. application Ser. No. 12/572,018, which is a continuation-in-part application that claims priority to U.S. application Ser. No. 12/054,712 filed on Mar. 25, 2008 which claims priority to U.S. Provisional Patent Application Ser. No. 60/908,707 filed on Mar. 29, 2007, all of which are incorporated herein by reference in their entirety.

FIELD OF THE INVENTION

The present invention relates to compositions and methods for preventing ocular angiogenesis and treating ocular angiogenesis-related diseases. In particular, the present invention is directed to parstatin peptides and their use to treat diabetic retinopathy, diabetic macular edema, age-related macular degeneration, retinopathy of prematurity and disorders associated with corneal neovascularization. In addition, this invention relates to compositions and methods for the prophylaxis and treatment of injuries in myocardium associated and caused by ischemia and reperfusion. The invention in particular relates to parstatin peptides and their therapeutic and prophylactic use for preventing, reducing and treating myocardial ischemia-reperfusion injury that may occur as a result of myocardial infarction, cardiac arrest, or in general after the disruption of blood flow to the heart.

BACKGROUND OF THE INVENTION

Pathologic or aberrant angiogenesis/neovascularization, aberrant remodeling, fibrosis and scarring and inflammation occur in association with retinal and ocular ischemic diseases such as age-related macular degeneration (AMD), diabetic retinopathy (DR) and in retinopathy of prematurity (ROP) and other developmental disorders (Eichler et al., 2006, Curr Pharm Des, 12: 2645-60) as well as being a result of infections and mechanical or chemical injury to the cornea and the eye in general (Ciulla et al., 2001, Curr Opin Opthalmol, 12: 442-9; Dart et al., 2003, Eye, 17: 886-92).

Diabetic retinopathy is a leading cause of blindness in adults of working age. The leading cause of vision loss for Americans under the age of 65 is diabetes; 16 million individuals in the United States are diabetic and 40,000 per year suffer from ocular complications of the disease, often a result of retinal neovascularization. DR, therefore, is a retinal microvascular disease that is manifested as a cascade of stages with increasing levels of severity and a worsening prognosis for vision. DR is broadly classified into 2 major clinical stages: nonproliferative diabetic retinopathy and proliferative diabetic retinopathy (PDR), where the term "proliferative" refers to the presence of preretinal neovascularization (PNV) emanating from the retina into the vitreous. Ocular neovascularization occurs in areas where capillary occlusions have developed, creating areas of ischemic retina and acting as a stimulus for neovascular proliferation that originate from pre-existing retinal venules at the optic disk and/or elsewhere in the retina posterior to the equator of the eye. Vitreous hemorrhage and tractional retinal detachment from PDR can cause severe vision loss (Boulton et al., 1997, Br J Opthalmol, 81: 228-223). Diabetic macular edema (DME) is another common cause of blindness (Levin, 2001, J Glaucoma 10:19-21; Stefansson et al., 1992, Am J. Opthalmol. 113:36-38). Clinical hallmarks of PDR include increased vascular permeability, leading to DME, and endothelial cell proliferation.

Age-related macular degeneration is a leading cause of vision loss in people over 65 years old. For example, AMD affects 12-15 million Americans over the age of 65 and causes vision loss in 10-15% of them. In contrast to ROP and PDR, in which neovascularization emanates from the retinal vasculature and extends into the vitreous cavity, AMD is associated with neovascularization originating from the choroidal vasculature and extending into the subretinal space. Choroidal neovascularization (CNV) causes severe vision loss in AMD patients because it occurs in the macula, the area of the retina responsible for central vision (Kitaoka et al., 1997, Curr Eye Res, 16:396-399).

Multiple theories exist, but the exact etiology and pathogenesis of AMD are still not well understood. Aging is associated with cumulative oxidative injury, thickening of Bruch's membrane and drusen formation. Oxidative stress results in injury to retinal pigment epithelial cells (RPE) and, in some cases, the choriocapillaris (Zarbin, 2004, Arch Opthalmol, 122: 598-614; Gorin et al., 1999, Mol V is, 5: 29). Injury to RPE likely elicits a chronic inflammatory response within Bruchs membrane and the choroid (Johnson et al., 2000, Exp Eye Res, 70: 441-9). This injury and inflammation fosters can potentiates retinal damage by stimulating CNV and atrophy (Zarbin, 2004, Arch Opthalmol, 122: 598-614; Witmer et al., 2003, Prog Retin Eye Res, 22: 1-29). CNV results in defective and leaky blood vessels (BV) that are likely to be recognized as a wound (Kent and Sheridan, 2003, Mol V is, 9: 747-55).

Retinopathy of prematurity (ROP) occurs most prominently in premature neonates. In various cases, the retina becomes completely vascularized at full term/near birth. In the premature baby, the retina remains incompletely vascularized at the time of birth. Rather than continuing in a normal fashion, vasculogenesis in the premature neonatal retina becomes disrupted. Maintaining the infants in incubators with high oxygen levels arrests the normal retinal vascular development and when they are removed to room air, this is a relative hypoxic environment and pathological angiogenesis results to compensate for the retinal oxygen deficiency due to insufficient vascularization. Abnormal new proliferating vessels develop at the juncture of vascularized and avascular retina. These abnormal new vessels grow from the retina into the vitreous, resulting in haemorrhage and tractional detachment of the retina (Neely et al., 1998, Am. J. Pathol, 153:665-670). It is estimated that visual impairment from this disease affects 3400 infants and causes blindness in 650 infants annually in the United States. Angiogenesis is the hallmark of this debilitating condition.

Others retinal diseases associated with retinal neovascularization include sickle cell retinopathy, retinal vein occlusion, certain inflammatory diseases of the eye, ocular tumorigenesis, Eale's disease, myopic choriodal neovascularization, and polypoidal choriodal vasculopathy. These, however, account for a much smaller proportion of visual loss caused by ocular neovascularization (Neely et al., 1998, American J. of Path. 153:665-670).

Corneal neovascularization, the abnormal formation of blood vessels in the cornea, is a common and serious complication of many corneal diseases and is a major cause of blindness that affects millions of people (Adamis, 2005, Retina, 25: 111-118). The condition is associated with severe visual impairment and is a high risk factor for graft rejection after allograft corneal transplantation. In addition, corneal neovascularization and subsequent opacification remain the most frequent causes of blindness after severe alkali burn trauma. To date, there are no pharmacological or surgical treatment options for the inhibition of corneal neovascularization that have been proven to be both safe and effective. Despite the routine use of topical steroids, the inflammatory response can lead to oedema, lipid deposition and corneal scarring that may not only significantly alter visual acuity, but also worsen the prognosis of subsequent penetrating keratoplasty. In addition, longer-term use of these drugs can lead to various adverse side effects such as cataracts, glaucoma, infection, and delayed corneal epithelial healing.

Angiogenesis is the process by which new blood vessels form (Carmeliet, 2005, Nature, 438: 932-936). In response to specific chemical signals, capillaries sprout from existing vessels, eventually growing in size as needed by the organism. Initially, endothelial cells, which line the blood vessels, divide in a direction orthogonal to the existing vessel, forming a solid sprout. Adjacent endothelial cells then form large vacuoles and the cells rearrange so that the vacuoles orient themselves end to end and eventually merge to form the lumen of a new capillary (tube formation).

Angiogenesis is stimulated by a number of conditions, such as in response to a wound, and accompanies virtually all tissue growth in vertebrate organisms such as mammals (Folkman, 2006, Annu Rev Med, 57: 1-18). In the normal adult, angiogenesis is tightly regulated, and is limited to wound healing, pregnancy and uterine cycling. Angiogenesis is turned on by specific angiogenic molecules such as basic fibroblast growth factor (bFGF), vascular endothelial growth factor (VEGF), angiogenin, transforming growth factor, tumor necrosis factor-alpha. (TNF-alpha) and platelet derived growth factor. On the other hand, angiogenesis can be suppressed by inhibitory molecules such as interferon-$\alpha$, thrombospondin-1, pigment epithelium derived factor (PEDF), angiostatin, and endostatin. It is the balance of these naturally occurring stimulators and inhibitors that controls the normally quiescent capillary vasculature. When this balance is upset, as in certain disease states, capillary endothelial cells are induced to proliferate, migrate and ultimately differentiate.

Angiogenesis plays a central role in a variety of diseases, including cancer and ocular neovascularization. Sustained growth and metastasis of a variety of tumors has also been shown to be dependent on the growth of new host blood vessels into the tumor in response to tumor derived angiogenic factors. Proliferation of new blood vessels in response to a variety of stimuli occurs as the dominant finding in the majority of eye diseases. In these diseases, tissue damage can stimulate release of angiogenic factors resulting in capillary proliferation (Gariano R F and Gardner T W, 2005, Nature, 438: 960-966). VEGF plays a dominant role in iris neovascularization and neovascular retinopathies. While reports clearly show a correlation between intraocular VEGF levels and ischemic retinopathic ocular neovascularization, FGF also likely plays an essential role. Basic FGF is known to be present in the normal adult retina, even though detectable levels are not consistently correlated with neovascularization. This may be largely due to the fact that FGF binds very tightly to charged components of the extracellular matrix and may not be readily available in a freely diffusible form that would be detected by standard assays of intraocular fluids. Furthermore, overexpression of bFGF in the eye does not stimulate neovascularization because it is sequestered (Ozaki et al., 1998, Am J Pathol, 153: 757-765), but bFGF does contribute to choriodal neovascularization when there is tissue disruption from the disease process itself or attempts at treatment (Yamada et al., 2000, J Cell Physiol, 185: 135-142).

Angiogenesis may be arrested or inhibited by interfering with the chemical signals that stimulate the angiogenic process. For example, angiogenic endothelial cells produce proteases to digest the basal lamina that surround the blood vessels, thus clearing a path for the new capillary. Inhibition of these proteases, or their formation, can prevent new vessels from forming Likewise, the endothelial cells proliferate in response to chemical signals. Particularly important proliferation signals include the VEGF and the bFGF families of proteins. Interference with these proliferation signaling processes can also inhibit angiogenesis.

Viable and approved current treatments for diseases related to ocular neovascularization are limited. The approved treatments for AMD are photodynamic therapy with VISUDYNE® (QLT/Novartis) and intravitreal injection of Macugen® (pegaptanib) (Eyetech/Pfizer) or Lucentis® (ranibizumab) (Genentech). Laser photocoagulation alone or photodynamic therapy with VISUDYNE® are therapies that involve laser-induced occlusion of the affected vasculature, which can result in localized damage to the retina. Macugen® (Eyetech/Pfizer) is an anti-VEGF aptamer that binds to VEGF165 preventing ligand-receptor interaction and is labeled for intravitreal injections every 4 weeks. Lucentis® (Genentech) is a humanized anti-VEGF antibody fragment that also binds directly to all isoforms of human VEGF and is labeled for intravitreal injections every 6 weeks. A variety of other pharmacologic therapies are undergoing clinical evaluation for AMD, such as RETAANE® 15 mg (anecortave acetate suspension, Alcon Research, Ltd.), Envision (squalamine, Genera), the VEGF R1R2 Trap, (Regeneron), Cand5 (anti-VEGF siRNA, Acuity), Sirna-027 (anti-VEGFR1 siRNA, SIRNA/Allergan), a topical receptor tyrosine kinase antagonist (TargeGen), sirolimus (rapamycin, MacuSight), etc.

Grid and pan retinal laser photocoagulation are the only proven options currently available for patients with diabetic macular edema or PDR, respectively. Multifocal laser photocoagulation may reduce retinal ischemia and inhibit angiogenesis by destroying healthy tissue and thus decreasing the total metabolic demand of the retina. Laser photocoagulation may also modulate the expression and production of various cytokines and trophic factors. Unfortunately, laser photocoagulation is a cytodestructive procedure and the visual field of the treated eye is irreversibly compromised. Surgical interventions, such as vitrectomy and removal of preretinal membranes, are widely used with or without laser treatment. Similar to the AMD trials, various pharmacologic agents are in clinical trials for DME, such as ARXXANT™ (ruboxystaurin mesylate, Lilly), RETISERT™ (fluocinolone acetonide, Bausch & Lomb), Posurdex (fluocinolone acetonide erodible implant, Occulex/Allergan), I-vation (nonerodible Dexamethasone implant, Occulex), Medidur (fluocinolone acetonide erodible implant, Alimera), etc. Intravitreal or periocular injection of triamcinolone acetonide, a corticosteroid (Kenalog®, Schering-Plough), and intravitreal Avastin® (anti-VEGF Mab (bevacizumab), Genentech) are also being used "off-label" for the treatment of both macular edema and wet AMD.

Anti-VEGF therapies represent a recent, significant advance in the treatment of exudative AMD. However, the phase III VISION Trial with PEGAPTANIB, a high affinity aptamer which selectively inhibits the 165 isoform of VEGF-A, demonstrated that the average patient continues to lose vision and only a small percent gained vision (Gragoudas et al., 2004, N Engl J Med, 351: 2805-16) Inhibition of all isoforms of VEGF-A (pan-VEGF inhibition) with the antibody fragment RANIBIZUMAB yielded much more impressive results (Brown et al., 2006, N Eng J Med, 355:1432-44; Rosenfeld et al., 2006, N Eng J Med 355:1419-31). The 2 year MARINA trial and the 1 year ANCHOR trial demonstrated that approximately 40% of patients achieve some visual gain. Although these results represent a major advance in our ability to treat exudative AMD, they also demonstrate that 60% of patients do not have visual improvement. Furthermore, these patients had to meet strictly defined inclusion and exclusion criteria. The results in a larger patient population may be less robust. In addition, adverse effects on neurons and vessels have been observed in primates after a single administration of the humanized anti-VEGF antibody (Bevacizumab) (Peters et al., 2007, Am J Opthalmol 91:827-31) and sporadic case reports of complications of anti-VEGF therapy related to regression of blood vessels, increased risk for stroke and myocardial infarction, and local side effects due to the intravitreal application mode have appeared (Fraunfelder et al., 2005, Drugs Today 41:703-9, Tobin et al., 2006, Insight 31:11-4, Rosenfeld et al., 2006, Opthalmol Clin NA 19:361-72, Baffert et al., 2006, Am J Physiol Heart Circ Physiol 290:H547-59, Hurwitz et al., 2004, Clin Colorectal Cancer 4 Suppl 2:S62-8). The limited efficacy and potential adverse effects of currently implemented therapies emphasize the need for alternative therapeutic strategies.

Ischemia-reperfusion injury (I/R injury) refers to an event in which the blood supply to a tissue is obstructed, such as myocardial infarction. Whenever there is a transient decrease or interruption of blood flow, the net injury is the sum of two components: the "direct" injury occurring during the ischemic interval and the "indirect" or reperfusion injury which follows. Reperfusion injury can be defined as the damage that occurs to an organ that is caused by the resumption of blood flow after an episode of ischemia. This damage is distinct from the injury resulting from the ischemia per se. One hallmark of reperfusion injury is that it may be attenuated by interventions initiated before or during the reperfusion. Reperfusion injury results from several complex and interdependent mechanisms that involve the production of reactive oxygen species, endothelial cell dysfunction, microvascular injury, alterations in intracellular $Ca^{2+}$ handling, changes in tissue metabolism, and activation of neutrophils, platelets, cytokines and the complement system. All of the deleterious consequences associated with reperfusion constitute a spectrum of reperfusion-associated pathologies that are collectively called reperfusion injury. Reperfusion injury can extend not only acutely, but also over several days following the tissue attack.

During blood vessel obstruction, the endothelial tissue lining the affected blood vessels becomes "sticky" and begins to attract circulating white blood cells (Tohoku, 2008, J Exp Med, 215: 257-266). The white cells bound to the endothelium eventually migrate into the cardiac tissue causing significant tissue destruction. Although acute myocardial infarction is not directly caused by inflammation, much of the underlying pathology and the damage that occurs after an acute ischemia-reperfusion injury is caused by acute inflammatory responses during reperfusion, the restoration of blood flow to the affected myocardium. White blood cells present to the area, by the newly returning blood release, a host of inflammatory factors such as interleukins as well as free radicals in response to tissue damage. The restored blood flow reintroduces oxygen within cells that damages cellular proteins, DNA and the plasma membranes. Damage of the cell membrane may in turn causes release of more free radicals signaling apoptosis. Leukocytes may also build up in small capillaries, obstructing them and leading to more ischemia.

Cardiovascular disease is the leading cause of death in the western world. Coronary artery disease can lead to prolonged or irreversible episodes of cardiac ischemia that result in myocardial infarction (MI) which is associated with a high rate of mortality. The reduced blood flow in heart diseases is typically caused by blockage of a vessel by an embolus (blood clot); the blockage of a vessel due to atherosclerosis; the breakage of a blood vessel (a bleeding stroke); the blockage of a blood vessel due to vasoconstriction such as occurs during vasospasms and possibly, during transient ischemic attacks (TIA) and following subarachnoid haemorrhage. Conditions in which ischemia occurs further include myocardial infarction; trauma; and during cardiac and thoracic surgery and neurosurgery (blood flow needs to be reduced or stopped to achieve the aims of surgery). Procedures that can cause myocardial ischemia include coronary thrombolysis, coronary angioplasty (with or without stent placement), and coronary artery bypass grafts. During myocardial infarct, stoppage of the heart or damage occurs which reduces the flow of blood to myocardium, and ischemia results. Cardiac tissue itself is also subjected to ischemic damage. During various surgeries, reduction of blood flow, clots or air bubbles generated can lead to significant ischemic damage of the myocardium.

During an ischemic event, there is a gradation of injury that arises from the ischemic site. Cells at the site of blood flow restriction, undergo necrosis and form the core of a lesion. A penumbra is formed around the core where the injury is not immediately fatal, but progresses slowly toward cell death. This progression to cell death may be reversed upon reestablishment of blood flow within a short time of the ischemic event. Timely reperfusion to reduce the duration of ischemia is the definitive treatment to prevent cellular injury and necrosis in an ischemic myocardium. Typically reperfusion, after a short episode of myocardial ischemia (up to 15 min), is followed by the rapid restoration of cellular metabolism and function. Even with the successful treatment of occluded vessels, a significant risk of additional tissue injury after reperfusion may still occur. If the ischemic episode has been of sufficient severity and/or duration to cause significant changes in the metabolism and the structural integrity of heart muscle, reperfusion may paradoxically result in a worsening of heart function, out of proportion to the amount of dysfunction expected simply as a result of the duration of blocked flow. Although the beneficial effects of early reperfusion of ischemic myocardium with thrombolytic therapy, PTCA, or CABG are now well established, an increasing body of evidence indicates that reperfusion also induces an additional injury to ischemic heart muscle, such as the extension of myocardial necrosis, i.e., extended infarct size and impaired contractile function and metabolism. Hearts undergoing reperfusion after transplantation also undergo similar reperfusion injury events.

Despite efforts towards the development of new therapies for the treatment of diseases and conditions such as heart failure and cardiac ischemia/reperfusion injury, this remains an unmet need for additional or alternative agents to treat or prevent the onset or severity of this condition (Ferdinandy et al., 2007, Pharmacol Rev, 59: 418-458). Current therapies include the use of vasodilators, anti-thrombotics/thrombolytics, beta-blockers and coronary artery bypass graft, which are used pre and post myocardial ischemia to maintain/restore coronary blood flow and limit oxygen demand.

SUMMARY OF THE INVENTION

The invention provides isolated parstatin peptides comprising amino acids 1-26 of SEQ ID NO: 1. In certain embodiments, the peptide is 26-35 amino acids in length. In certain embodiments, the peptide is 26-30 amino acids in length.

The invention provides pharmaceutical compositions including an isolated parstatin peptide comprising amino acids 1-26 of SEQ ID NO: 1. In certain embodiments, the peptide is 26-35 amino acids in length. In certain embodiments, the peptide is 26-30 amino acids in length.

The invention provides methods of treatment of aberrant ocular angiogenesis in a subject by administration of an isolated parstatin peptide comprising amino acids 1-26 of SEQ ID NO: 1 to the subject, whereby aberrant angiogenesis is treated. In certain embodiments, the peptide is 26-35 amino acids in length. In certain embodiments, the peptide is 26-30 amino acids in length. In certain embodiments, the method further includes identifying a subject suffering from or suspected of suffering from aberrant ocular angiogenesis. In certain embodiments, the method further includes monitoring a subject for treatment of aberrant ocular angiogenesis. In certain embodiments, administration of an isolated parstatin peptide includes contacting an eye of the subject with of an isolated parstatin peptide.

The invention provides methods of prevention or treatment of myocardial ischemic injury in a subject by administration of a parstatin peptide amino acids 1-26 of SEQ ID NO: 1 to the subject, whereby myocardial ischemic injury is prevented or treated. In certain embodiments, the peptide is 26-35 amino acids in length. In certain embodiments, the peptide is 26-30 amino acids in length. In certain embodiments, myocardial ischemic injury includes ischemic injury related to surgery. In certain embodiments, myocardial ischemic injury comprises ischemia-reperfusion injury. In certain embodiments, the method further includes identifying a subject suffering from or suspected of suffering from myocardial ischemic injury. In certain embodiments, the method further includes monitoring a subject for treatment of myocardial ischemic injury. In certain embodiments, the method further includes identifying a subject suffering from, suspected of suffering from, or prone to suffering from myocardial ischemic injury. In certain embodiments, the method further includes monitoring a subject for treatment of myocardial ischemic injury. In certain embodiments, the method includes administration of an isolated parstatin peptide comprises contacting a heart of the subject with of an isolated parstatin peptide.

DEFINITIONS

Figure 1:
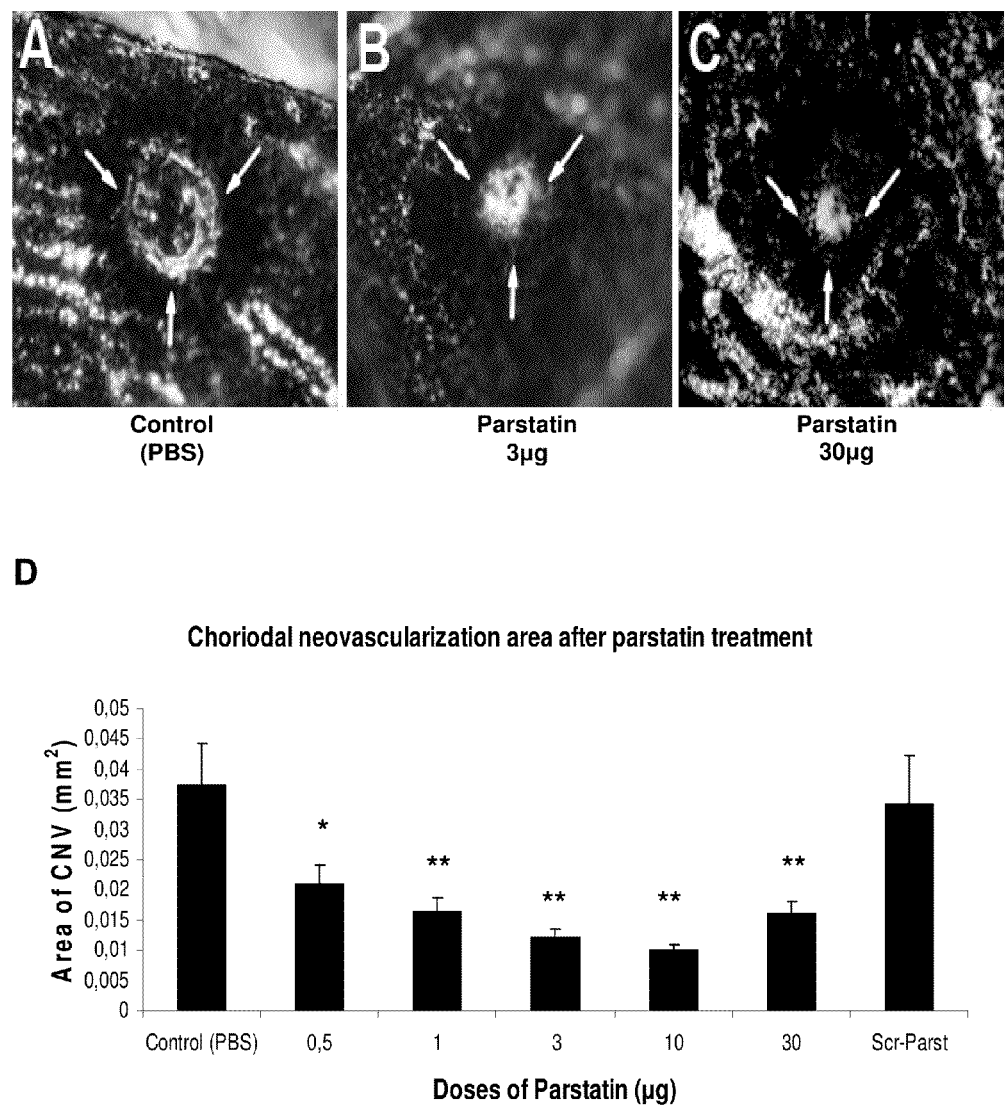
FIG. 1. Intravitreous injections of parstatin peptides suppress choriodal neovascularization. Laser-induced ruptures of Bruch's membrane were performed in C57BL/6 mice. Intravitreal injections of 1 µl solutions of different doses of parstatin (0.5-30 µg) or vehicle alone, (control, PBS) were administered immediately after laser treatment and 7 days after laser treatment. Choriodal neovascularization (CNV) was assessed 14 days after laser treatment. Mice were perfused with fluorescein-labeled destran and choriodal flat mounts were prepared and examined by fluorescence microscopy. Compared to eyes injected with PBS (A, control), those injected with 3 µg (B) or 30 µg (C) showed proportionally smaller areas of CNV. D, The area of CNV at each rupture site was measured by image analysis and the mean area of CNV per eye was calculated to give a single experimental value. In graph D, the bars show the mean (±SE) for each group calculated from 12 experimental values and confirm that compared to eyes injected with PBS, the mean area of CNV was significantly less, in a dose dependent-manner, in eyes injected with parstatin. Mice treated with scrambled parstatin (Scr-Parst, 30 µg) presented mean area of CNV similar to that obtained in control mice. In graph E, intravitreal injections of 1 µl solution of hydrophobic parstatin (1-26) fragment (10 µg) or vehicle alone (DMSO) were administered immediately after laser treatment and 7 days after laser treatment. CNV was assessed 14 days after laser treatment. Compared to eyes injected with DMSO, those injected with hydrophobic parstatin (1-26) fragment exhibited significantly less mean area of CNV. *$P<0.05$; $P<0.01$ FIG. 2. Intravitreous injections of parstatin suppress ischemia-induced retinal neovascularization. Newborn C57BL/6 mice were placed in 75% oxygen at postnatal day $(P)_7$. At P12 they were returned to room air. At P17, mice were given an intravitrous injection of rat anti-mouse PECAM-1 antibody and euthanized after 12 hours. Retinas were removed, washed and incubated in goat anti-rat antibody conjugated with Alexa 488 and retinal flat mounts were examined by fluorescence microscopy. Intravitreal injections of 1 µl solutions of different doses of parstatin (0.5-30 µg) or vehicle alone, (control, PBS) were administered on P12 and P15. Retinas from mice treated with parstatin (B) appeared to have much less neovascularization than retinas from mice treated with PBS (A). Image analysis confirmed that compared to eyes injected with PBS, eyes injected with parstatin (n=12 for each) showed a dose-dependent reduction in mean (±SE) area of neovascularization per retina (C). Mice treated with scrambled parstatin (Scr-Parst, 3 µg) presented mean area of retinal neovascularization similar to that obtained in control mice. $P<0.01$ FIG. 3. Subconjunctival injections of parstatin suppress corneal neovascularization. Chemical burn-induced corneal traumas were performed in Sprague Dawley rats. Cauterization was performed by application of 75% silver nitrate and 25% potassium nitrate to center of the corneas. Subconjunctival injections of 2×20 µl (two injections per eye) of different doses of parstatin (50-200 µg) or vehicle alone, (control, PBS) were administered immediately after cauterization. Corneal neovascularization was assessed 7 days after cauterization. Compared to eyes injected with PBS (A, control), those injected with 2×75 µg (B) or 2×100 µg (C) showed smaller areas of corneal neovascularization. D, The length of corneal vessels was measured by image analysis. Compared to eyes injected with PBS, eyes injected with parstatin (n=12 for each group) showed a dose-dependent reduction in mean (±SE) length of vessels per cornea. E, The area of corneal neovascularization was measured by image analysis. Compared to eyes injected with PBS, eyes injected with parstatin (n=12 for each group) showed a dose-dependent reduction in mean (±SE) area of neovascularization per cornea. Mice treated with scrambled parstatin (Scr-Parst, 2×100 µg) presented mean length and area of CNV similar to that obtained in control rats. *$P<0.05$; **$P<0.01$.
Figure 1:
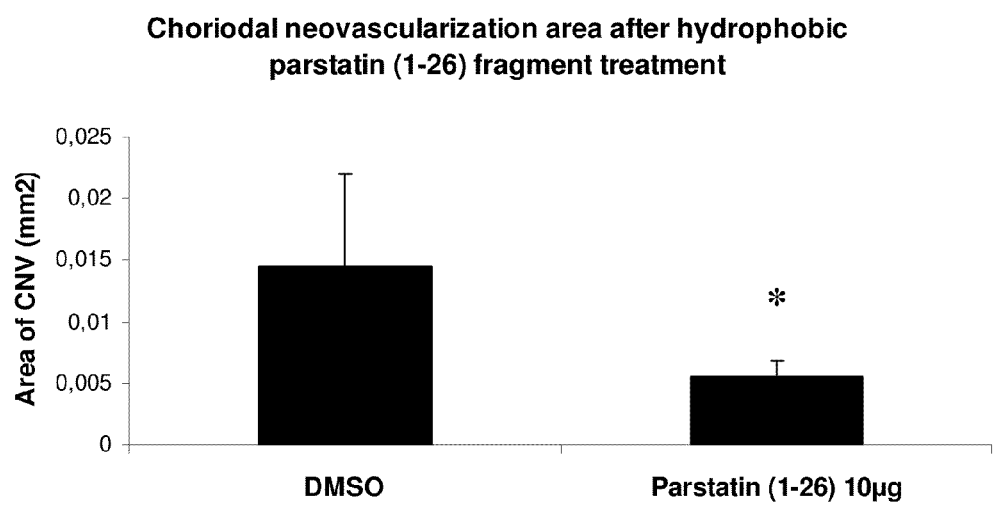

The present invention includes methods and compositions for preventing, ameliorating, and/or treating angiogenesis related diseases, diseases having an angiogenic component, and processes mediated by undesired and uncontrolled angiogenesis by administrating to a human or animal with the undesired angiogenesis a composition comprising a substantially purified parstatin or parstatin derivatives in a dosage sufficient to prevent or inhibit angiogenesis. The present invention further includes methods and compositions for preventing, ameliorating, and/or treating myocardial ischemia/reperfusion related diseases or heart or coronary diseases having an ischemia/reperfusion component. Parstatin peptides can be administered alone or in conjunction with other agents for the prevention, amelioration, and/or treatment of angiogenesis related diseases or myocardial ischemia/reperfusion related diseases. The other agents can be anti-angiogenic agents. Alternatively, the agents can function to prevent, ameliorate, or treat disease by distinct methods, e.g., anti-proliferative agents for the treatment of cancer or anti-inflammatory agents for the treatment of arthritis or vasodilators, anti-thrombotics/thrombolytics and beta-blockers to maintain/restore coronary blood flow and limit oxygen demand.

The present invention provides methods and compositions for treating diseases and processes mediated by endothelial cell dysfunction and cardiovascular complications by administrating to a human or animal a composition comprising a substantially purified parstatin peptide or parstatin derivatives in a therapeutically effective dose to prevent, treat, or ameliorate one or more symptoms associated with endothelium dysfunction diseases or angiogenesis, and prevent or treat conditions characterized by cardiovascular complications.

The term "amelioration" refers to a reduction of at least one sign and/or symptom of a specific disease or condition. Treatment refers to reduction of at least one sign and/or symptom of a disease or condition to reduce or eliminate at least one sign and/or symptom of the disease or condition, or to prevent progression of the disease or condition. Prevention, amelioration, and treatment need not be considered separate interventions, but instead can be considered a continuum of therapeutic interventions.

The term "angiogenesis" is understood as a physiological process involving the growth of new blood vessels from pre-existing vessels, including vasculogenesis. Vasculogenesis is the term used for spontaneous blood-vessel formation. Angiogenesis is a normal process in growth and development, as well as in wound healing. However, this is also a fundamental step in the transition of tumors from a dormant state to a malignant state. Angiogenesis is promoted by biological signals known as angiogenic growth factors that activate receptors present on endothelial cells present in pre-existing venular blood vessels. The activated endothelial cells begin to release enzymes called proteases that degrade the basement membrane in order to allow endothelial cells to escape from the original (parent) vessel walls. The endothelial cells then proliferate into the surrounding matrix and form solid sprouts or processes connecting neighboring vessels. As sprouts extend toward the source of the angiogenic stimulus, endothelial cells migrate in tandem, using integrin adhesion molecules. These sprouts then form loops to become a full-fledged vessel lumen as cells migrate to the site of angiogenesis. Sprouting occurs at a rate of several millimeters per day, and enables new vessels to grow across gaps in the vasculature.

As used herein, "angiogenesis associated diseases" particularly diseases related to excessive and aberrant angiogenesis include, but are not limited to, ocular diseases associated with angiogenesis including, but not limited to retinal and ocular ischemic diseases such as macular degeneration including age-related macular degeneration (AMD), diabetic retinopathy (DR), neovascular glaucoma, retinopathy of prematurity (ROP) and other developmental disorders, a result of ocular infections, mechanical or chemical injury to the cornea and the eye in general. Angiogenesis associated diseases can also occur outside of the eye and include, but are not limited to chronic inflammation, arthritis, rheumatoid arthritis, osteoarthritis, ulcerative colitis, Crohn's disease, psoriasis, cancer, atherosclerosis, restenosis, intimal hyperplasia, or pulmonary hypertension. Many ischemia related conditions are associated with insufficient angiogenesis including, but not limited to, coronary artery disease, stroke, and chronic wounds.

In addition, the invention includes compositions in which the parstatin peptide or a part of it is conjugated with a "cell-penetrating moiety" or "membrane-tethering moiety". Cell-penetrating moiety is a compound which mediates transfer of a substance from an extracellular space to an intracellular compartment of a cell. Cell-penetrating moieties shuttle a linked substance (e.g., parstatin peptides, fragments, and analogs) into the cytoplasm or to the cytoplasmic space of the cell membrane. Membrane-tethering moiety is a compound which associates with or binds to a cell membrane. Thus, the membrane-tethering moiety brings the substance (e.g., parstatin peptides, fragments, and analogs) to which the membrane-tethering moiety is attached in close proximity to the membrane of a target cell. For example, a cell penetrating or membrane-tethering moiety is a hydrophobic moiety. Cell-penetrating and membrane-tethering moieties include a lipid, cholesterol, phospholipids, steroid, sphingosine, ceramide, or a fatty acid moiety. The cell-penetrating or membrane-tethering moiety is attached to the C-terminal amino acid, the N-terminal amino acid, or to an amino acid between the N-terminal and C-terminal amino acid of the parstatin or parstatin fragment.

As used herein, "changed as compared to a control reference sample" is understood as having a level or activity of an analyte, or in a whole organism change of physical characteristics or signs or symptoms of a disease, to be detected at a level that is statistically different than a sample from a normal, untreated, or control sample. Methods to select and test control samples are within the ability of those in the art. Control samples typically include a cell or an animal of the same type that has not been contacted with an active agent or been subjected to a particular treatment, and has optionally been contacted with a carrier or subjected to a sham treatment. Control samples also include a cell or an animal not subjected to an agent or treatment to induce a specific disease or condition.

A "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide. Conservative changes can further include substitution of chemically homologous non-natural amino acids (i.e. a synthetic non-natural hydrophobic amino acid in place of leucine, a synthetic non-natural aromatic amino acid in place of tryptophan).

"Contacting a cell" is understood herein as providing an agent to a cell, in culture or in an animal, such that the agent can interact with the surface of the cell, potentially be taken up by the cell, and have an effect on the cell. The agent can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "detecting", "detection" and the like are understood that an assay performed for identification of a specific analyte in a sample or a change in a subject of at least one sign or symptom of a disease, expression of a protein or gene, including a reporter construct. The amount of analyte detected in the sample or change of behavior in a subject can be none or below the level of detection of the assay or method.

The term "detectable label" is understood as a chemical modification, binding agent, or other tag that can be readily observed, preferably in a quantitative manner, such as a fluorescent tag that has specific wavelengths of absorption and emission to allow detection of the compound associated with the detectable label.

The terms "disease" or "condition" are commonly recognized in the art and designate the presence of at least one sign and/or symptom in a subject or patient that are generally recognized as abnormal. Diseases or conditions may be diagnosed and categorized based on pathological changes. Signs may include any objective evidence of a disease such as changes that are evident by physical examination of a patient or the results of diagnostic tests that may include, among others, laboratory tests. Symptoms are subjective evidence of disease or a patient condition, e.g., the patient's perception of an abnormal condition that differs from normal function, sensation, or appearance, which may include, without limitations, physical disabilities, morbidity, pain, and other changes from the normal condition experienced by a subject.

The terms "drug", "therapeutic agent", and the like as used herein refer to a chemical entity or biological product, or combination of chemical entities or biological products, administered to a subject to treat or prevent or control a disease or condition. The drug or therapeutic agent can be formulated with one or more pharmaceutically acceptable carriers. Therapeutic agents of the instant invention, e.g., parstatin peptides, can be co-administered with other drugs or therapeutic agents. "Co-administering," as used herein refers to the administration with another agent, either at the same time, in the same composition, at alternating times, in separate compositions, or combinations thereof.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as an improvement of symptoms, a cure, a reduction in disease signs or symptoms, extension of life, improvement in quality of life, or other effect generally recognized as positive by medical doctors familiar with treating the particular type of disease or condition.

The term "effective amount" refers to a dosage or amount that is sufficient to reduce, halt, or slow tumor progression to result in alleviation, lessening or amelioration of symptoms in a patient or to achieve a desired biological outcome, e.g., slow or stop tumor growth or reduction or disappearance of a tumor. "Pharmaceutically acceptable excipients or vehicles" include, for example, water, saline, glycerol, ethanol, etc. Additionally, auxiliary substances, such as wetting or emulsifying agents, pH buffering substances, and the like, may be present in such vehicles.

As used herein, "ischemia/reperfusion injury" or "I/R injury," sometimes simply referred to as "I/R" refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function. Ischemia/reperfusion injury can occur after a spontaneously occurring event, e.g., stroke, heart attack; or a planned event, e.g., any of a number of surgical interventions.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in a heterologous system). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 80-90%, or about 90-95%, up to 99-100% pure) of cellular or organismal material naturally associated with it, and thus is distinguished from naturally occurring polypeptide. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. Isolated cells can be further modified to include reporter constructs or be treated with various stimuli to modulate expression of a gene of interest.

As used herein, "kits" are understood to contain at least the non-standard laboratory reagents for use in the methods of the invention, such as a parstatin polypeptide or amino acid coding sequence. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

The term "parstatin peptide" refers to a peptide, preferably a substantially isolated or purified peptide, that is preferably about 41 amino acids and approximately 4.5 kDa in size and corresponds to the cleaved peptide of human PAR1 (Genbank Accession Number AF019616) with the sequence: MGPRRLLLVAACFSLCGPLLSARTRAR-RPESKATNATLDPR (SEQ ID NO: 1). Such peptides are naturally generated by cleavage of the N-terminal domain of the protease activated receptor-1 (PAR-1). Cleavage and release of the N-terminal domain results in the generation of a new N-terminus on the receptor, activating the receptor. Parstatin is predicted to be less than 41 residues in length because of an initial hydrophobic domain of approximately 21 to 23 amino acids (MGPRRLLLVAACFSLCGPLLSAR (amino acids 1-23 of SEQ ID NO: 1) that may represent a putative signal sequence. Indeed, PAR1 belongs to the small subgroup of G protein-coupled receptors (5-10%) possessing N-terminal signal peptides. Signal peptides have been shown to facilitate export of many secretory proteins across eukaryotic endoplasmic reticulum and are believed to be cleaved-off after mediating the endoplasmatic reticulum targeting/insertion process. However, this may not always be the case. Interestingly, parstatin contains an asparagines-linked (Asn35) glycosylation site, which may prevent proteolysis of signal sequence. In addition, some evidence that parstatin may be released from thrombin-activated platelets has also been reported (Ramachandran et al, 1994, Thromb Haemost, 78: 1119-1124; Furman et al, 2000, Thromb Haemost, 84: 897-

903). In certain embodiments of the invention, a parstatin peptide can include amino acids 1-26 of SEQ ID NO: 1, which is also referred to as the hydrophobic fragment of parstatin.

As demonstrated herein, parstatin peptides (e.g., full length parstatin (1-41) and the parstatin hydrophobic peptide (1-26)) are potent inhibitors of angiogenesis, endothelial cell growth, migration, and differentiation. As further demonstrated herein, the same parstatin peptides promote endothelial cell apoptosis and block the angiogenic process (e.g., ocular angiogenesis). In addition, the same parstatin peptides have been demonstrated to be effective in the prevention and treatment of myocardial ischemia/reperfusion injury. Moreover, parstatin peptides are demonstrated to work across species with mouse parstatin having an effect on human cells and tissues, and both mouse and human parstatin having an effect on rat cells and tissues.

The present invention is contemplated to include any derivatives of parstatin that are active in vitro and in vivo. The present invention includes the entire parstatin peptide (full length SEQ ID NO: 1), derivatives of the parstatin peptide, and biologically-active fragments of the parstatin peptide, including truncations of the N- and/or C-terminus of SEQ ID NO: 1, and internal deletions. The term "parstatin peptides" includes longer peptides with N- and/or C-terminal extensions or insertions in the 4.5 kDa peptide of SEQ ID NO: 1, and modified peptides and proteins that have a substantially similar amino acid sequence, and which have the ability to modulate endothelial cell functions and physiological and pathological processes. The term "parstatin peptides" also includes shorter peptides with one or more amino acids is removed from either or both N- and C-terminal (e.g., deletion of amino acids 27-41) or from internal regions in the 4.5 kDa peptide of SEQ ID NO: 1 and modified peptides that have a substantially similar amino acid sequence, and which have the ability to modulate endothelial cell functions and physiological and pathological processes.

For example, substitutions of amino acids, wherein the replacement of an amino acid with a structurally or chemically similar amino acid does not significantly alter the structure, conformation or activity of the peptide (i.e., a conservative substitution) is well known in the art. As demonstrated herein, mouse parstatin has an effect on both human and rat cells and tissues. Human parstatin has an effect on rat cells and tissues. Sequence alignments demonstrate that human and mouse parstatin (N-terminus of Accession No. AAB38308.1, incorporated herein by reference) are 63% identical and 80% similar over the 41 amino acid length of the peptide sequences. The N-terminal 41 amino acids of the thrombin receptor of *Cricetulus longicaudatus* (long-tailed dwarf hamster, Accession No. CAA43957.1) are 68% identical and 85% similar to human parstatin. The N-terminal 41 amino acids of rat thrombin receptor (Accession No. P26824) are 67% identical and 75% similar to human parstatin over amino acids 1-37. The N-terminal 41 amino acids of the thrombin receptor of *Bos Taurus* (cow, Accession No. A7YY44) are 63% identical and 68% similar over the first 41 amino acids. The N-terminal 41 amino acids of the thrombin receptor of *Macaca mulatta* (rhesus monkey, Accession No. XP_001106136) are 92% identical and 92% similar over the first 41 amino acids. (All Accession Nos. as of the date of filing of the priority application are incorporated herein by reference.) An alignment of the sequences generated using ClustalW2 is presented below and can be used to identify amino acids likely more or less tolerant to mutation.

| | | SEQ ID |
|---|---|---|
| hu-man | MGPRRLLLVAACFSLCGPLLSARTRARRPESKAT NATLDPR | 41 1 |
| mon-key | MGPRRLLLVAACLCLCGPLLSARTRARRPASKAT NATLDPR | 41 5 |
| mouse | MGPRRLLIVALGLSLCGPLLSSRVPMSQPESERT DATVNPR | 41 4 |
| rat | MGPRRLLLVAVGLSLCGPLLSSRVPMRQPESERM YATPYAT | 41 6 |
| ham-ster | MGPQRLLLVAAGLSLCGPLLSSRVPVRQPESEMT DATVNPR | 41 3 |
| bo-vine | MGPRWLLLLWAAGLGLCSPLVSARTRGPRPGTDPT *:: * : .:*:*. :* :. NGTLGPR .* . | 41 7 |

For example, mutation of amino acids conserved across all species which are indicated with an * (e.g., amino acids 1-3, 6-7, 10, 15-16, 18-19, 21, 23, 29, and 37) would likely be more disruptive to function than mutations at amino acids that are not conserved across species. Mutations at non-conserved amino acids (e.g., amino acids 5, 9, 11-12, 14, 17, 20, 22, 24, 25-27, 30, 33-35, 38-39, and 41) would likely be more well tolerated. Conservative amino acid substitutions would likely be tolerated at positions indicated with : or . (e.g., positions 4, 8, 13, 17, 20, 22, 28, 31, 32, 36, 40).

Parstatin peptides having mutations or alterations that do not eliminate parstatin peptide function are also included within the scope of the invention. Such mutations or alterations can alter properties of the peptide such as bioavailability or allow for modification of the peptide with various groups. Groups may be to allow for detection of parstatin peptides (e.g., radioactive or fluorescent label) or to change or augment the activity of the peptide (e.g., a chemotherapeutic agent). Such substitutions fall within the scope of the invention. These include peptides with parstatin activity that have amino acid substitutions or have sugars or other molecules attached to amino acid functional groups. Methods for site directed mutagenesis are well known and saturation mutational analysis is a common method, especially in short peptides that can be generated by synthetic methods. Moreover, as demonstrated herein, parstatin peptides have activity across species demonstrating that sequence variation is tolerable and does not completely disrupt the activity of parstatin peptides. Moreover, sites of variation between species can provide an indication of sites that can be altered while retaining function.

Parstatin peptides have at least 30%, 40%, 50%, 60%, 70%, 80%, 85%, 90%, 95%, or more activity as compared to the peptide of SEQ ID NO: 1 in at least one of the assays taught herein. Such assays are routine in the art. In an embodiment, the assay in an angiogenesis assay. In an embodiment, the assay is a cell proliferation assay. In an embodiment, the assay is a cell mitogenesis assay. In an embodiment, the assay is a cell migration assay. In an embodiment, the assay is a cell differentiation assay. In an embodiment, the assay is an apoptosis assay. In an embodiment, the assay is a cell cycle progression assay. In an embodiment, the assay is a kinase activation assay. In an embodiment, the assay is an ischemia/reperfusion assay.

In certain embodiments, a parstatin peptide includes 5 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, or 41 consecutive amino acids of SEQ ID NO: 1. In certain embodiments, a parstatin peptide is an 18 amino acid fragment of SEQ ID NO: 1 including amino acids 24-41 of SEQ ID NO: 1. In certain embodiments, a parstatin peptide is a 26 amino acid fragment of SEQ ID NO 1 including amino acids 1-26 of SEQ ID NO: 1. In certain embodiments, a parstatin peptide includes a parstatin peptide sequence covalently linked, e.g., through a peptide bond, to a non-parstatin peptide sequence.

The invention includes compositions in which the parstatin molecule, fragments, and analogs are conjugated with sugar molecules. Glycosylation is a universal characteristic of proteins in nature, which determines their physicochemical and biological properties. Design and synthesis of glycopeptides is a topic of intense research in the last years, since the carbohydrate modification can improve the pharmacokinetic characteristics, or otherwise enhance or alter the biologic activity and can be used as a tool to study the biologic functions.

Parstatin peptides of the present invention can be made by automated peptide synthesis methodologies well known to one skilled in the art. Alternatively, parstatin, of the present invention may be isolated from larger proteins, such as human PAR-1, rat PAR-1, mouse PAR-1, and primate PAR-1 proteins that share a common or similar N-terminal amino acid sequence.

Parstatin peptides can be produced upon the proteolysis of PAR-1 by proteases such as thrombin, plasmin, activated protein C, or metalloprotease-1. Parstatin peptides can also be produced from recombinant sources, from genetically altered cells implanted into animals, and from platelets and cell cultures as well as other sources. It is anticipated that parstatin is made in cells of the nervous system and tumors. Parstatin can be isolated from body fluids including, but not limited to, serum, urine, and ascites, or synthesized by chemical or biological methods (e.g. cell culture, recombinant gene expression, peptide synthesis, and in vitro enzymatic catalysis of precursor molecules to yield active parstatin). Recombinant techniques include gene amplification from DNA sources using the polymerase chain reaction (PCR), and gene amplification from RNA sources using reverse transcriptase/PCR. The specific method of making the parstatin peptides of the invention is not a limitation of any of the compositions or methods of the invention.

"Peptide", "polypeptide", "protein", and the like are understood as two or more naturally occurring or synthetic amino acids joined by an amide linkage. Optionally the peptide further includes one or more modifications such as modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins, Structure and Molecular Properties, 2nd ed., T. E. Creighton, W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-646 (1990); Rattan et al., Ann N.Y. Acad. Sci. 663: 48-62 (1992)).

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, intrathecal, intracranial, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

The term "prevention" refers to a reduction in the chance that a subject is prone to or will suffer from a particular disease or condition. The chance of a subject suffering from a particular disease or condition can be determined by a trained individual, such as a physician. For example, a subject suffering from cardiac ischemia of sufficient duration will likely suffer from reperfusion injury, a subject undergoing certain types of surgery may suffer from ischemia reperfusion injury, particularly cardiac ischemia-reperfusion injury. Prevention can include administration of a therapeutic agent one or more times to a subject, e.g., a long standing prophylactic regimen to prevent aberrant angiogenesis, or a single dose in response to an acute event such as ischemia. Prevention can include administration of one or more doses of a compound of the instant invention prior to an event that can result in an ischemia/reperfusion injury, for example, certain types of surgery. For example, a compound of the instant invention can be delivered 1 hour or less, 2 hours or less, 3 hours or less, 4 hours or less, 6 hours or less, 8 hours or less, 12 hours or less, 16 hours or less, 20 hours or less, 24 hours or less, 36 hours or less, or 48 hours or less before the expected ischemic event. Prevention can include a reduction in the level of signs or symptoms observed of the condition and need not completely eliminate all signs or symptoms of disease, e.g., reduce the area or severity of damage as a result of ischemia-reperfusion injury. Prevention can include a delay in the first onset of signs or symptoms of a disease or condition and need not prevent signs or symptoms from ever being present.

Prevention of a disease or condition can include treatment prior to a subject undergoing a procedure, e.g., a surgical procedure, that may or may not induce a condition that can be ameliorated or prevented by a parstatin peptide. For example, various types of surgery can cause ischemia in the myocardial tissue during the surgery. However, the extent of ischemia and related damage depends on a number of factors including, but not limited to, the subject and the surgeon(s). A parstatin peptide can be administered prior to, during, or after surgery to prevent ischemic injury such as ischemia-reperfusion injury that may or may not occur in relation to the surgery on the particular individual.

"Providing," refers to obtaining, by for example, buying or making the, e.g., polypeptide, drug, polynucleotide, probe, and the like. The material provided may be made by any known or later developed biochemical or other technique. For example, polypeptides may be obtained from cultured cells or chemical synthesis methods. The cultured cells, for example, may comprise an expression construct comprising a nucleic acid segment encoding the polypeptide.

A "sample" as used herein refers to a biological material that is isolated from its environment (e.g., blood or tissue from an animal, cells, or conditioned media from tissue culture) and is suspected of containing, or known to contain an analyte. A sample can also be a partially purified fraction of a tissue or bodily fluid. A reference sample can be a "normal" sample, from a donor not having the disease or condition fluid. A reference sample can also be from an untreated donor or cell culture not treated with an active agent (e.g., no treatment or administration of vehicle only) or not subjected to conditions to induce a disease state. A reference sample can also be taken at a "zero time point" prior to contacting the cell with the agent to be tested.

As used herein, "small molecule" is understood to refer to a chemical compound having a molecular weight of 1500 Da or less, 1250 Da or less, 1000 Da or less, 750 Da or less, or 500 Da or less. In certain embodiments, "small molecule" does not include peptide or nucleic acid molecules.

A "subject" as used herein refers to living organisms. In certain embodiments, the living organism is an animal. In certain preferred embodiments, the subject is a mammal. In certain embodiments, the subject is a domesticated mammal Examples of subjects include humans, non-human primates, dogs, cats, mice, rats, cows, horses, goats, and sheep. A human subject may also be referred to as a patient.

A subject "suffering from or suspected of suffering from" a specific disease, condition, or syndrome has at least one risk factor and/or presents with at least one sign or symptom of the disease, condition, or syndrome such that a competent individual would diagnose or suspect that the subject was suffering from the disease, condition, or syndrome. Methods for identification of subjects suffering from or suspected of suffering from various diseases associated with excess angiogenesis is within the ability of those in the art. Methods of identifying specific genetic or lifestyle predispositions (e.g., age, diabetes) to diseases associated with excess angiogenesis is well within the ability of those of skill in the art. Methods of identifying subjects undergoing various surgeries that may result in cardiac ischemia is well within the ability of those of skill in the art. Subjects suffering from, and suspected of suffering from, a specific disease, condition, or syndrome are not necessarily two distinct groups.

"Substantial sequence homology" means at least about 60% homology, at least about 70% homology, at least about 80% homology, preferably at least about 90% homology between amino acid residue sequence to the reference sequence. "Substantial sequence identity" means at least about 60% identity, at least about 70% identity, at least about 80% identity, preferably at least about 90% identity, or at least about 95% identity to the reference sequence (e.g., parstatin peptide sequences, particularly human parstatin peptide sequences).

In addition, the invention encompasses compositions in which the parstatin sequence contains a peptidomimetic. For example, the invention includes parstatin compounds in which one or more peptide bonds have been replaced with an alternative type of covalent bond, which is not susceptible to cleavage by peptidases (a "peptide mimetic" or "peptidomimetic"). Where proteolytic degradation of peptides following injection into the subject is a problem, replacement of a particularly sensitive peptide bond with a non-cleavable peptide mimetic renders the resulting peptide more stable and thus more useful as a therapeutic. Such mimetics, and methods of incorporating them into peptides, are well known in the art. Similarly, the replacement of an L-amino acid residue (e.g., with a D-amino acid) renders the peptide less sensitive to proteolysis.

Additionally, parstatin compounds of the invention can be synthesized as retro-inverso isomers, which include peptides of reverse sequence and chirality (Jameson et al., Nature, 368: 744-746, 1994; Brady et al., Nature, 368: 692-693, 1994). The net result of combining D-enantiomers and reverse synthesis is that the positions of carbonyl and amino groups in each amide bond are exchanged, while the position of the side-chain groups at each alpha carbon is preserved. For example, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art.

"Therapeutically effective amount," as used herein refers to an amount of an agent which is effective, upon single or multiple dose administration to the cell or subject, decreasing at least one sign or symptom of the disease or disorder, or prolonging the survivability of the patient with such a disease or disorder beyond that expected in the absence of such treatment.

An agent can be administered to a subject, either alone or in combination with one or more therapeutic agents, as a pharmaceutical composition in mixture with conventional excipient, e.g., pharmaceutically acceptable carrier.

The pharmaceutical agents may be conveniently administered in unit dosage form and may be prepared by any of the methods well known in the pharmaceutical arts, e.g., as described in Remington's Pharmaceutical Sciences (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

The compounds of the invention can, for example, be administered by injection, intravenously, intraarterially, subdermally, intraperitoneally, intramuscularly, intrathecally, intracranially, or subcutaneously; or orally, buccally, nasally, transmucosally, intravaginally, cervically, topically, in an ophthalmic preparation, or by inhalation, with a dosage ranging from about 0.001 to about 100 mg/kg of body weight, or according to the requirements of the particular drug and more preferably from 0.5-10 mg/kg of body weight. Methods of administration by injection or infusion can be performed using a pump, for example an implantable pump or an external pump attached to a permanent catheter. The methods herein contemplate administration of an effective amount of compound or compound composition to achieve the desired or stated effect. Typically, the pharmaceutical compositions of this invention will be administered once a day, once a week, every two weeks, once a month, or more or less frequently, depending on the specific needs of the subject to be treated. The specific pharmacokinetic and pharmacodynamic properties of the composition to be administered will effect dosing. Such administration can be used as a chronic or acute therapy. The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of one or more signs or symptoms of cancer.

Pharmaceutical compositions of this invention comprise compounds of the invention or a pharmaceutically acceptable salt thereof. Further, pharmaceutical compositions of the instant invention can be administered with other pharmaceutical agents used for the treatment of cancer or other hyperplastic disorders.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

The term "therapy" refers to a process that is intended to produce a beneficial change in the condition of a mammal, e.g., a human, often referred to as a patient. A beneficial change can, for example, include one or more of restoration of function, reduction of symptoms, limitation or retardation of progression of a disease, disorder, or condition or prevention, limitation or retardation of deterioration of a patient's condition, disease or disorder.

Cells and/or subjects may be treated and/or contacted with one or more anti-angiogenic or other therapeutic treatments including, surgery, chemotherapy, radiotherapy, gene therapy, immune therapy or hormonal therapy, or other therapy recommended or proscribed by self or by a health care provider.

"Therapeutically effective amount," as used herein refers to an amount of an agent which is effective, upon single or multiple dose administration to the cell or subject, in prolonging the survivability of the patient with such a disorder beyond that expected in the absence of such treatment.

Compositions described herein may be administered, for example, systemically, intratumorally, intravascularally, to a resected tumor bed, orally, or by inhalation.

As used herein, "treating, preventing or alleviating angiogenic related disease," refers to the prophylactic or therapeutic use of the therapeutic agents described herein.

Treatment, amelioration, and/or prevention of a disease is practiced on a subject first identified as being prone to or suffering from a disease or condition. During and after treatment, amelioration, and prevention of a disease or condition, a subject is typically monitored for signs or symptoms of the disease or condition.

The present invention also includes diagnostic methods and kits for detection and measurement of parstatin in biological fluids and tissues, and for localization of parstatin in tissues. The diagnostic method and kit can be in any configuration well known to those of ordinary skill in the art. The present invention also includes antibodies, which can be polyclonal antibodies or monoclonal antibodies, specific for the parstatin. Kits can further include packaging material and/or instructions for use of the components of the kits.

The present invention also includes oligonucleotide aptamers, which can be DNA aptamers or RNA aptamers, specific for the parstatin. The antibodies and aptamers specific for parstatin can be used in diagnostic kits to detect the presence and quantity of parstatin as index of activated PAR-1 in vivo which is diagnostic or prognostic for the occurrence or recurrence of cancer or other disease mediated by angiogenesis. Antibodies and aptamers specific for parstatin can also be administered to a human or animal against endogenous parstatin, thereby stimulating angiogenesis in situations where promotion of angiogenesis is desirable, such as in wound healing and non-healing ulcers.

The present invention also includes parstatin peptides and fragments that are labeled isotopically or with other molecules for use in the detection and visualization of parstatin binding sites with state of the art techniques, including, but not limited to, positron emission tomography, autoradiography, flow cytometry, radioreceptor binding assays, and immunohistochemistry. Such peptides and fragments can be conveniently included in kits, optionally containing instructions for use.

The parstatin peptides of the invention are useful for treating, preventing or ameliorating one or more symptoms associated with diseases and conditions characterized by aberrant angiogenic activity and/or endothelial cell dysfunction. Such diseases and conditions include, but not limited to, angiogenesis-related tumor growth and metastasis, ocular neovascular diseases, rheumatoid arthritis, chronic inflammation, myocardial ischemia/reperfusion injury, restenosis, pulmonary hypertension, atheroscherosis, intima hyperplasia. For example, such methods are carried out by contacting a cell or a tissue undergoing pathological angiogenesis with parstatin. The method involves administration to a subject, e.g., a human patient, in which such treatment or prevention is desired, a parstatin peptide in an amount sufficient to reduce the severity of the pathology in the subject, i.e., in a therapeutically effective dose. The present invention also includes pharmaceutical compositions containing any parstatin peptide and a pharmaceutically acceptable carrier.

The invention also includes nucleic acid sequences that correspond to and code for the bioactive peptide molecules of the invention, to monoclonal and polyclonal antibodies that bind specifically to such peptides molecules and DNA or RNA oligonucleotides (aptamers) that bind specifically to such peptide molecules. The biologically active peptide molecules, nucleic acid sequences corresponding to the peptides, antibodies and aptamers that bind specifically to the peptides of the present invention are useful for modulating endothelial processes in vivo, and for diagnosing and treating endothelial cell-related diseases, for example by gene therapy.

Nucleic acid sequences that correspond to, and code for, parstatin and parstatin analogs can be prepared based upon the knowledge of the amino acid sequence, and the art recognized correspondence between codons, and amino acids.

Nucleic acid sequences are synthesized using automated systems well known in the art. Either the entire sequence may be synthesized or a series of smaller oligonucleotides are made and subsequently ligated together to yield the full length sequence. Alternatively, the nucleic acid sequence may be derived from a gene bank using oligonucleotides probes based on the N-terminal amino acid sequence and well known techniques for cloning genetic material.

The present invention also includes the detection of parstatin in body fluids and tissues for the purpose of diagnosis or prognosis of angiogenesis-mediated diseases such as cancer, cardiovascular diseases, ocular diseases, and arthritis. Antibodies and aptamers that specifically bind to parstatin can be used in diagnostic methods and kits that are well known to those of ordinary skill in the art to detect or quantify the parstatin in a body fluid or tissue. Results from these tests can be used to diagnose or predict the occurrence or recurrence of a cancer and other angiogenesis mediated diseases and pathophysiological processes wherein PAR-1 is involved.

The present invention further includes the detection of parstatin binding sites and receptors in cells and tissues. The present invention also includes methods of treating or preventing angiogenic diseases and processes including, but not limited to, arthritis, diabetic retinopathy and tumors by stimulating the production of parstatin, and/or by administrating substantially purified parstatin polypeptides, parstatin agonists, or parstatin antagonists. It is to be understood that the parstatin can be of animal, particularly mammalian, for example of human in origin. Parstatin can also be produced synthetically by chemical reaction or by recombinant techniques in conjunction with expression systems. Parstatin can also be produced by enzymatically cleaving different molecules, including parstatin precursors or peptides, containing sequence homology or identity with segments of parstatin to generate peptides having anti-angiogenesic activity.

Passive antibody therapy using antibodies that specifically bind parstatin can be employed to modulate endothelial-dependent processes such as reproduction, development, and wound healing and tissue repair. Antibodies specific for parstatin, parstatin peptides, and parstatin analogs are made according to techniques and protocols well known in the art. The antibodies may be either polyclonal or monoclonal. The antibodies are utilized in well know immunoassay formats, such as competitive and non-competitive immunoassays, including ELISA, sandwich immunoassays, and radioimmunoassay (RIAs), to determine the presence or absence of the endothelial proliferation inhibitors of the present invention in body fluids. Examples of body fluids include but are not limited to blood, serum, peritoneal fluid, pleural fluid, cerebrospinal fluid, uterine fluid, saliva and mucus.

Oligonucleotide therapy using aptamers that specifically bind parstatin can be employed to modulate endothelial-dependent processes such as reproduction, development, wound healing, and tissue repair. The term "aptamers" refers to nucleic acid molecules (DNA or RNA) having specific binding affinity to molecules through interactions other than classic Watson-Crick base pairing. Aptamers, like peptides generated by phage display or monoclonal antibodies are capable of specifically binding to selected targets and modulating the target's activity or binding interactions, e.g., through binding aptamers, may block their target's ability to function. Aptamers specific for parstatin and parstatin analogs are made according to techniques and protocols well known in the art. A typical aptamer is 10-15 kDa in size (20-45 nucleotides), binds its target with nanomolar to subnanomolar affinity, and discriminates against closely related targets.

The peptides, nucleic acid sequences, antibodies, and aptamers of the present invention are useful for diagnosing and treating endothelial cell-related diseases and disorders. A particularly important endothelial cell process is angiogenesis, the formation of blood vessels. Angiogenesis-related diseases may be diagnosed and treated using the endothelial cell proliferation inhibiting proteins of the present invention, i.e., parstatin peptides and analogs. Angiogenesis-related diseases include, but are not limited to, angiogenesis-dependent cancer (solid tumors, blood born tumors such as leukemias, ands tumor metastases; benign tumors, for example hemangiomas, acoustic neuromas, neurofibromas), rheumatoid arthritis, psoriasis, ocular angiogenic diseases (diabetic retinopathy, retinopathy of prematurity, macular degeneration, corneal graft rejection, neovascular glaucoma, retrolental fibroplasias), myocardial angiogenesis, plaque neovascularization, and wound granulation.

The parstatin endothelial cell proliferation inhibiting peptides of the present invention are useful in the treatment of disease of excessive or abnormal stimulation of endothelial cells. These diseases include, but are not limited to, intestinal adhesions, atherosclerosis, scleroderma and hypertrophic scars, i.e., keloids. They are also useful in the treatment of diseases that have angiogenesis as a pathologic consequence such as cat scratch disease (*Rochele minalia* quintosa) and ulcers (*Helobacter pylori*).

Conversely, blockade of parstatin receptors with parstatin analogs which act as receptor antagonists as well as blockade of parstatin molecules with antibodies or aptamers, which specifically bind and inhibit parstatin biological activity, may promote endothelialization and vascularization. Such effects may be desirable in situations of inadequate vascularization of the uterine endometrium and associated infertility, wound repair, healing of cuts and incisions, treatment of vascular problems in diabetics, especially retinal and peripheral vessels, peripheral angiopathies, especially peripheral ischemic vascular disorders, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

The amino acid sequence of the peptide is known and the parstatin peptide can be synthesized by any technique well known in the art, as exemplified by "Solid Phase Peptide Synthesis: A Practical Approach" E. Atherton and R. C. Sheppard, IRL Press, Oxford, England. Similarly, multiple fragments can be synthesized which are subsequently linked together to form larger fragments. These synthesis peptide fragments can also be made with amino acid substitutions at specific locations in order to test for agonistic and antagonistic activity in vitro and in vivo. Peptide fragments that possess high affinity binding to tissues can be used to isolate the parstatin receptor on affinity columns. Isolation and purification of the parstatin receptor is a fundamental step towards elucidating the mechanism of action of parstatin. This facilitates development of drugs to modulate the activity of the parstatin receptor, the final pathway to biological activity. Isolation of the receptor enables the construction of nucleotide probes to monitor the location and synthesis of the receptor, using in situ and solution hybridization technology.

The synthetic peptide fragments of parstatin have a variety of uses. The peptide that binds to the parstatin receptor with high specificity and avidity can be detectably labeled, e.g., radiolabeled or fluorescently labeled, and employed for visualization and quantitation of binding sites using known techniques, such as membrane binding techniques. This application provides important diagnosis and research tools. Knowledge of the binding properties of the parstatin receptor facilitates investigation of the transduction mechanisms linked to the receptor. In addition, labeling these peptides with short lived isotopes enables visualization of receptor binding sites in vivo using positron emission tomography or other modern radiographic techniques in order to locate tumors or cardiovascular complications with parstatin binding sites.

Systematic substitution of amino acids within parstatin or its fragments yields high affinity peptide agonists and antagonists to the parstatin receptor that enhance or diminish parstatin binding to its receptor. Such agonists are used to suppress the growth of micrometastases, thereby limiting the spread of cancer. Antagonists to parstatin are applied in situations of inadequate vascularization, to block the inhibitory effects of parstatin and possibly promote angiogenesis. This treatment may have therapeutic effects to promote wound healing in diabetics.

According to the present invention, parstatin can be used in combination with other compositions and procedures for the treatment of diseases.

The peptides and peptide fragments with the parstatin activity described above can be provided as isolated and substantially purified peptides and peptide fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal, or parenteral (e.g., intravenous, intraspinal, subcutaneous, or intramuscular) route. In addition, the parstatin peptide may be incorporated into biodegradable polymers allowing for sustained release of compound, the polymers being implanted in the vicinity of where drug delivery is desired, for example, at the site of a tumor or implanted so that the parstatin is slowly released systemically. Osmotic minipumps may also be used to provide controlled delivery of high concentrations of parstatin through cannulae to the site of interest, e.g., directly into a metastatic growth or into the vascular supply to that tumor.

Cytotoxic and antiangiogenic compounds are used in medical devices, e.g., as drug eluting stents to prevent restenosis and intimal hyperplasia. For example, a vascular endoprosthetic device, e.g., a stent includes parstatin. The composition is impregnated in the device or the device is coated with the parstatin.

The dosage of the parstatin of the present invention will depend on the disease state or condition being treated and other clinical factors such as weight and condition of the human or animal and the route of administration of the compound. For treating humans or animals, between approximately 0.5 mg/kilogram to 500 mg/kilogram of the parstatin peptide can be administered. A more preferable range is 1 mg/kilogram to 100 mg/kilogram with the most preferable range being from 1 mg/kilogram to 50 mg/kilogram. Depending upon the half-life of the parstatin peptide in the particular animal or human, the parstatin peptide can be administered between several times per day to once a week. It is to be understood that the present invention has application for both human and veterinary use. The methods of the present invention contemplate single as well as multiple administrations, given either simultaneously or over an extended period of time.

Formulations suitable for parenteral administration include aqueous and non-aqueous sterile injection solutions which may contain anti-oxidants, buffers, bacteriostatics and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly those mentioned above, the formulations of the present invention may include other agents conventional in the art having regard to the type of formulation in question.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

"At least" a particular value is understood to mean that value or more. For example, "at least 2" is understood to be the same as "2 or more" i.e., 2, 3, 4, 5, 6, 7, 8, 9, 10, 11, 12, 13, 14, 15, etc.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references, patents, patent applications, and Accession Numbers as of the filing date of the priority application referred to herein are specifically incorporated by reference.

DETAILED DESCRIPTION OF THE INVENTION

The invention includes a class of bioactive peptide molecules that have the ability to modulate endothelial cell functions and physiological and pathological processes. These peptides are collectively referred to as parstatin peptides. The invention further includes methods of use of parstatin peptides. Parstatin peptide molecules of the invention have particularly the ability to inhibit endothelial cell growth, migration, and differentiation, to induce endothelial cell apoptosis, to block angiogenesis process, and to protect against myocardial ischemia-reperfusion injury.

Protease-activated receptors (PARs) consists of a novel family of G protein-coupled receptors which can be activated by proteolytic cleavage of their N-terminal extracellular domain (Ossovskaya and Bunnett, 2004). PAR1 is the first member of this family to be cloned in which the extracellular amino terminus is cleaved to expose a new amino terminus that is involved in receptor activation (Vu et al., 1991). Subsequently, three other members of this receptor family have been identified, designated as PAR2, PAR3 and PAR4. Proteolytic cleavage at the R41/S42 bond of human PAR1 by thrombin releases a 41 amino acid peptide and unveils a tethered peptide ligand with the recognition sequence SFLLRN (SEQ ID NO: 8). This sequence binds to conserved regions in the second extracellular loop of the cleaved receptor, resulting in the initiation of signal transduction. It is generally accepted that thrombin is the principal physiological regulator of PAR1 but there is strong evidence that other proteases, such as plasmin, factor Xa, activated protein C, as well as matrix metalloprotease-1, can contribute to the activation of this receptor (Leger et al., 2006).

Despite the wealth of information relating to the role of thrombin and PAR1 in physiology and disease states, the information regarding the biological role of cleaved peptides upon activation of PAR1 is limited. After proteolytic cleavage of the N-terminal region of PAR1 at the activation site, the released peptide of 41 amino acids peptide can exert biological functions. The name of parstatin has recently been suggested for this peptide released in the milieu upon PAR1 activation (Zania et al., 2009, J Pharmacol Exp Ther, 328: 378-389; U.S. Patent Publication 20080242613). Parstatin suppressed both basic angiogenesis and that stimulated by bFGF and VEGF in chick CAM model and in the rat aortic ring model of angiogenesis. Parstatin also inhibited endothelial cell migration and capillary-like network formation on the Matrigel and fibrin angiogenesis models in vitro.

Treatment of endothelial cells with parstatin resulted in inhibition of cell growth by inhibiting the phosphorylation of ERK1/2 in a specific and reversible fashion and by promoting cell cycle arrest and apoptosis, through a mechanism involving activation of caspases. The molecular mechanism by which parstatin could exert its effects is still unknown, and the invention is not limited by the mechanism of action of a parstatin peptide. However, parstatin is able to cross the plasma membrane, highlighting a crucial effect for the hydrophobic domain of the peptide to exert its biological functions on endothelial cells. Based on these findings, parstatin is useful for treating angiogenesis-related diseases, such as angiogenesis-dependent cancer and ocular diseases. Current protein-based therapies for ocular angiogenesis inhibit only VEGF and because of their large size are administered by repeated intraocular injections. Therefore, parstatin which blocks both angiogenic activity of VEGF and bFGF may provide greater efficacy for the treatment of ocular neovascularization than targeting VEGF alone. In addition, agents that can be delivered by topical administration to the cornea could offer substantial advantages beyond a less invasive delivery mode, for example the potential for a superior safety profile if systemic exposure were meaningfully reduced. Because parstatin is a cell penetrating peptide, it may be effective by topical application onto the eye.

It was recently demonstrated that parstatin, the N-terminal cleavage product of PAR1, is an effective agent for cardioprotection during ischemia and reperfusion of the rat myocardium (Strande et al., 2009 Cardiovasc Res, 83: 325-334). It was also shown that parstatin causes vasodilation in isolated rat coronary arterioles. Both cardioprotection and vasodilatory properties of parstatin are dependant on nitric oxide synthase (NOS) and $K^+$-ATP channels. In particular, these data implicate the up-regulation of endothelial derived NOS and increases in bioavailable nitric oxide (NO) as an important mechanism behind parstatin's cardioprotective and vasodilatory effects. Collectively, the results of these studies in rat hearts and coronary vessels strongly support the concept that parstatin serves a protective role during ischemia-reperfusion by protecting endothelial function. Since the cardioprotective effects of parstatin occurred in the absence of hemodynamic changes, there is an exciting opportunity to develop parstatin to protect against myocardial and microvascular injury in the clinical setting.

Therefore, there is still a well defined unmet need to develop further therapeutic agents that target other steps in the development of ocular angiogenesis. Without wishing to be bound by theory, we suggest that a therapy that simultaneously targets multiple components and mediators of the choroidal, retinal, or corneal neovascular response has the potential to be a more effective therapy than "single-target" therapy. First, the growth of choroidal blood vessels involves an orchestrated interaction among many mediators, not just VEGF, offering an opportunity to modulate or inhibit the entire process (Gragoudas et al., 2004, N Engl J Med, 351: 2805-16). Thus, combined blockage of VEGF and bFGF angiogenic activity may provide greater efficacy for the treatment of ocular neovascularization than targeting VEGF alone. Second, exudative AMD is comprised of vascular and extravascular components. The vascular component involves vascular endothelial cells (EC), EC precursors, and pericytes. The extravascular component, which appears to be the largest component, is composed of inflammatory, glial and retinal pigment epithelium cells and fibroblasts. Tissue damage can result from either component. These aspects of the pathologic process are not addressed by current anti-VEGF treatments. Targeting additional elements of the angiogenic cascade associated with AMD could provide a more effective and synergistic approach to therapy.

To date, there is no specific treatment for myocardial ischemia/reperfusion injury. Several drugs have been proposed to ameliorate the experimental injury caused by I/R, as manifested by reduced histological damage and faster recovery of myocardial function in different animal models. These include anti-oxidants, calcium channel blockers, vasoactive substances, growth factors, anti-inflammatory agents and more. However, those drugs that have been studied in clinical trials showed no benefit, and their use in myocardial ischemia-reperfusion injury has not been approved.

Provided herein are parstatin peptide compositions, especially parstatin 1-41 and parstatin 1-26, and methods and uses for such peptides in the prevention, amelioration, and treatment of one or more diseases or conditions not limited to, opthalmological conditions, diseases of excess angiogenesis, and myocardial ischemia/reperfusion injury related to naturally occurring events (e.g., cardiac arrest, occlusion, surgery).

In opthalmology, many ocular neovascular diseases are characterized by pathological invasion of new blood vessels into the structure of the eye, such as the retina and cornea. They are the most common cause of blindness and comprise approximately twenty eye diseases. Such diseases include, but are not limited to, age related macular degeneration, both wet and dry, diabetic retinopathy, and retinopathy of prematurity.

Many types of surgery present the possibility of ischemia/reperfusion injury, for example, in cardiology, where ischemia/reperfusion injury in myocardium occurs following many medical treatment and procedures, such as successful balloon angioplasty or thrombolysis. Administration of the compounds of the present invention can prevent ischemia/reperfusion injury by ameliorating or eliminating the damage caused by reperfusion injury, for example by administration of the compound prior to the ischemic event. Administration of the compounds of the invention during or after the event can ameliorate or treat the damage caused by ischemia/reperfusion injury.

The invention is further illustrated by the following examples, which are not meant to be construed in any as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Parstatin Peptides Synthesis and Compositions

Parstatin peptides used in our assays were synthesized in the core peptide facility of Peptide Specialty Laboratories GmbH (Heidelberg, Germany) or Bio-Synthesis Inc., (Lewisville, Tex.) or at the Protein and Nucleic Acid Shared Facility at the Medical College of Wisconsin. Synthesized peptides were purified by HPLC technology, were characterized by mass spectrometry technology and were sequenced. The synthesized peptides were as follow:

Human parstatin, which corresponds to 1-41-amino acids cleaved N-terminal fragment of human PAR1. Sequence: MGPRRLLLVAACFSLCGPLLSARTRAR-RPESKATNATLDPR (SEQ ID NO: 1) (molecular weight of 4468 Da).

Scrambled human parstatin, which contains to randomly rearranging the amino acid sequence to human parstatin. Sequence: LRTNASLLVPFLTARAKSSGTREAADP-PRLMCLRPLARRCG (SEQ ID NO: 2) (molecular weight of 4468 Da).

Human short parstatin, which corresponds to 24-41 of SEQ ID NO: 1 (18 amino acids) amino acid sequence of human parstatin. Sequence: TRARRPESKATNATLDPR (molecular weight of 2041 Da).

Human hydrophobic parstatin, which corresponds to 1-26 amino acid sequence of human parstatin (SEQ ID NO: 1). Sequence: MGPRRLLLVAACFSLCGPLLSARTRA (molecular weight of 2772 Da).

Example 2

Parstatin (1-41) Inhibits Angiogenesis In Vivo

The in vivo chick chorioallontoic membrane (CAM) angiogenesis model was used to evaluate the effect of parstatin (1-41) in angiogenesis. On incubation day 9 of fertilized chicken eggs, an O-ring (1 cm$^2$) was placed on the surface of the CAM and the vehicle or the indicated substances were placed inside this restricted area. After 48 h, CAMs were fixed in saline-buffered formalin, photographed, and analyzed using the Scion Image software (Scion Image Release Beta 4.0.2 software; Scion Corporation, Frederick, Md.). Image analysis was performed on at least 18 eggs for each group. Vessel number and length were evaluated by pixel counting, and the results expressed as mean percentage of control±SE. Statistical analyses were performed using a Student's t test.

Parstatin (1-41) was a very potent antiangiogenic substance. The application of human parstatin on CAM of chick embryo, at concentration of 10 nmoles, resulted in a significant inhibition of the basal level of angiogenesis that occurs in CAMs. This inhibitory effect was dose-dependent and not toxic for the chick embryo, at concentrations up to 300 nmoles. Interestingly, the anti-angiogenic effect of parstatin was more pronounced when angiogenesis was stimulated by growth factors such as bFGF or VEGF.

Mouse parstatin also inhibited vessel formation in the CAM model but to a lesser extent than human parstatin. These data demonstrate that parstatin peptides are capable of working across species (i.e., human and mouse on chicken) and that some sequence variation is tolerable while retaining activity of the parstatin peptides as antiangiogenic agents. The application of short and scrambled parstatins, at concentration similar to that of human or mouse parstatins (10 nmoles), did not cause any significant effect. These results demonstrate the sequence specific, dose specific effect of both human and mouse parstatin peptides on vascular growth in an accepted angiogenesis model.

Example 3

Parstatin (1-41) Inhibits Angiogenesis in Rat Aortic Ring Assay

The recognition that angiogenesis in vivo involves not only endothelial cells but also their surrounding cells, has led to development of angiogenic assays using organ culture methods. Of these, the rat aortic ring assay has become the most widely used.

Freshly cut aortic rings obtained from 5- to 10-week-old Fischer 344 male rats were embedded in collagen gels and transferred to 16-mm wells (4-well NUNC dishes) each containing 0.5 ml serum-free endothelial basal medium (EBM, Clonetics Corporation) alone or supplemented with VEGF or bFGF. The angiogenic response of aortic cultures was measured in the live cultures by counting the number of neovessels over time using art accepted methods. Mean number of microvessels±SE was determined Statistical analysis was performed using unpaired two-tailed t-test.

Parstatin (1-41) inhibited microvessel formation in a dose-dependant manner, with complete inhibition at a 10 mM concentration. This inhibitory effect was evident either in basal conditions or in VEGF- or bFGF-induced angiogenesis. Again, the ability of parstatin to function across species is noted. Human parstatin effectively inhibits angiogenesis in rat tissue in a non-species specific, dose dependent manner.

Example 4

Parstatin (1-41) Inhibits Capillary Tube-Like Formation by Endothelial Cells

Primary human umbilical vein endothelial cells (HUVEC cells) were obtained from freshly delivered umbilical cords from caesarean births and were grown in M199 medium with 20% fetal bovine serum (FBS) supplemented with endothelial cell growth supplement and heparin. One of the most specific tests for angiogenesis is the measurement of the ability of endothelial cells to form capillary-like structures (i.e., tube formation). Tube formation is a multi-step process involving cell adhesion, migration and differentiation. Tube formation can be enhanced by the use of Matrigel or fibrin clots to coat plastic culture dishes and it is an accepted model of angiogenesis.

Matrigel™ (Becton Dickinson Labware, NJ, USA) is a mixture of basement membrane components extracted from the Englebreth-Holm-Swarm tumor. It has been demonstrated that endothelial cells attach, migrate, and assemble to form tube-like structures resembling capillaries within 18 hours of plating. Matrigel (250 µl) was added to each well of a 24-well plate and allowed to polymerize. A suspension of 40,000 HUVEC cells in M199 medium containing 5% FBS was added into each well coated with Matrigel™.

Cells were treated with increasing concentrations of human parstatin, scrambled parstatin, or short parstatin (24-41). After 18 hours of incubation, the medium was removed, and the cells were fixed and stained, and tube-like structures were quantitated.

When parstatin (1-41) was tested in the Matrigel™ model, it exhibited a significant inhibitory effect on the rate and extent of tube formation. At concentrations ranging from 0.3 to 10 µM, parstatin (1-41) caused a dose-dependent inhibition of tube formation by endothelial cells plated on medium containing 5% serum. Mouse parstatin was effective in inhibiting tube formation by human cells.

The ability of endothelial cells to form three-dimensional structures was analyzed using a Fibrin gel in vitro angiogenesis assay kit (Chemicon International Inc. Temecula, Calif.). Fibrin gels were formed in 48-well plates by mixing fibrinogen and thrombin solutions, according to the manufacturer's instructions. Cells (40,000 cells/well) were then added and cultured in medium containing 2% FBS for 18 h. After the addition of a second layer of fibrin gel, endothelial cells sandwiched within fibrin gels were cultured in serum-free medium containing 0.5% bovine serum albumin (BSA) and the combination of VEGF/bFGF for 24 h. Where indicated, parstatin or other peptides were added. Capillary-like networks were photographed and measured.

Similar results were evident in a fibrin in vitro angiogenesis model as in the tube formation model, where endothelial cells were cultured in a sandwich mode between two fibrin gels, and formed capillary-like tubes in 3 dimensions. The total capillary tube length induced by VEGF and bFGF was significantly reduced by parstatin (1-41). Control scrambled parstatin and short parstatin did not affect the ability of endothelial cells to form capillary-like networks in either model. Exposure of endothelial cells to mouse parstatin (1-41) resulted in a less pronounced, but still significant, inhibitory effect. These data further demonstrate the effectiveness of parstatin peptides as anti-angiogenic agents both within and across species.

Example 5

Parstatin (1-41) Inhibits Cell Migration of Endothelial Cells

HUVEC cell migration was assessed using a modified Boyden's chamber assay, i.e., in Transwell cell culture chambers (Corning Life Sciences, Acton, Mass.). Briefly, polycarbonate filters with 8 nm pores were used to separate the upper and the lower chambers. Cells were added to the upper compartment at a density of 10,000 cells/100 µl in serum-free medium containing 0.5% BSA and incubated for 6 h. Directional migration (chemotaxis) in the lower chamber was induced by addition of medium containing 5% FBS to the lower chamber. Where indicated, parstatin or other peptides were added to lower chamber.

Cells on the filters were fixed and stained. The non-migrated cells (cells in upper surface) were removed by wiping with cotton swabs. The cells on the lower surface were counted manually under a microscope in six predetermined fields. Parstatin (1-41) attenuated chemotactic cell migration through the microporous membrane in response to serum. When human parstatin was combined with 5% FBS, the number of migrated cells was reduced in a concentration-dependent manner Again, scrambled parstatin and short parstatin (24-41) were without effect. Mouse parstatin (1-41) caused a significant inhibitory effect, but to a lower extent as compared to human parstatin (1-41). These data demonstrate that parstatin can have an anti-angiogenic effect by decreasing cell migration, a required step in angiogenesis.

Example 6

Parstatin (1-41) Inhibits Growth of Endothelial Cells

Cell proliferation was evaluated using a 3-(4,5-dimethyl-2-yl)-2,5-diphenyltetrazolium bromide (MTT, Sigma-Aldrich, St. Louis, Mo.) assay. Endothelial cells (10,000/well) were seeded in 24-well tissue culture plates and incubated with growth medium for 24 h. Cells were then treated with the vehicle or the indicated peptides in medium containing 5% FBS for 1 to 3 days. After 24, 48, or 72 hours, MTT solution (5 mg/ml) was added to each well and incubated for 3 h at 37° C. The blue formazan crystals were solubilized by addition of DMSO and absorbance at 450 nm was recorded using a 96-well plate reader.

Endothelial cell number doubled every 18 to 26 h over the 72-h period. In the presence of parstatin (1-41), the rate of endothelial cell growth was significantly decreased. HUVEC cell proliferation was essentially blocked by 10 µM parstatin. This inhibitory effect of parstatin was dose-dependent with half-maximal inhibitory concentration at approximately 3 µm.

Figure 4:
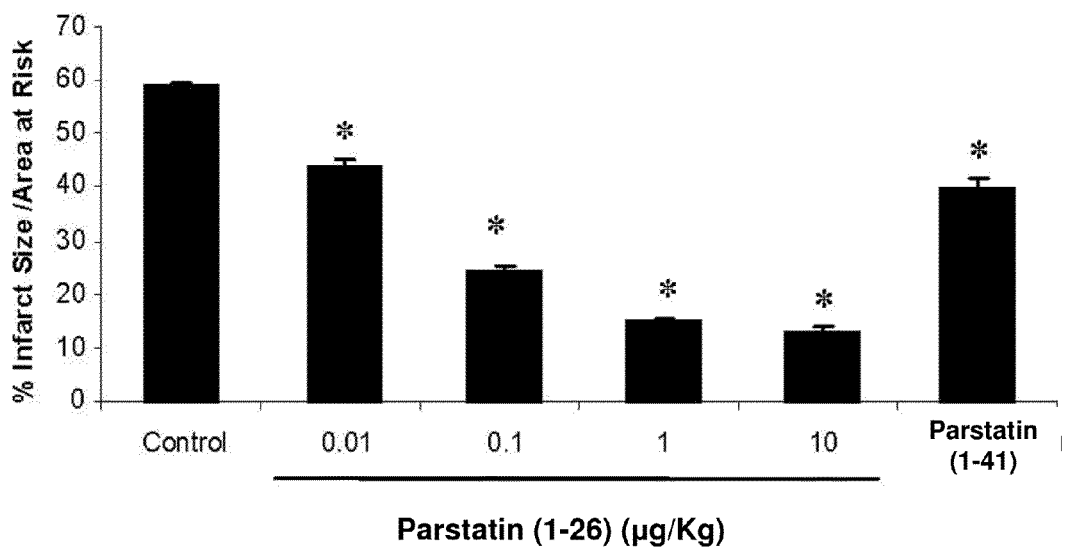
FIG. 4. Analysis of cardioprotective effects of hydrophobic parstatin fragment 1-26 in rat myocardial ischemia-reperfusion injury model in vivo. Male Sprague Dawley rats underwent 30 min of regional ischemia followed by 120 min of reperfusion. Parstatin (parstatin 1-41) or hydrophobic parstatin fragment 1-26 (parstatin 1-26), which corresponds to the 1-26 amino acid sequence of parstatin, were administered intravenously 15 min prior to ischemia, 15 min after the onset of ischemia, or 10 seconds after the onset of reperfusion. At the end of reperfusion the ischemia-reperfusion injury was assessed and the Area at Risk and infarct-to risk ratios were determined by computerized planimetry. A, Dose response analysis of hydrophobic parstatin fragment 1-26 and comparison with optimal protective dose of full parstatin (10 µg/kg). Rats were treated with either vehicle (control) or different doses of hydrophobic parstatin fragment 1-26 or parstatin administered as an IV bolus 15 min prior to ischemia. B, Time response analysis of hydrophobic parstatin fragment 1-26. Rats were treated with either vehicle (control) or hydrophobic parstatin fragment 1-26 (1 µg/kg) as an IV bolus either 15 min prior to ischemia or 15 min after onset of ischemia or 10 sec after onset of reperfusion. Results are expressed as mean±SE, n=6 rats/group. *P<0.05.
Figure 4:
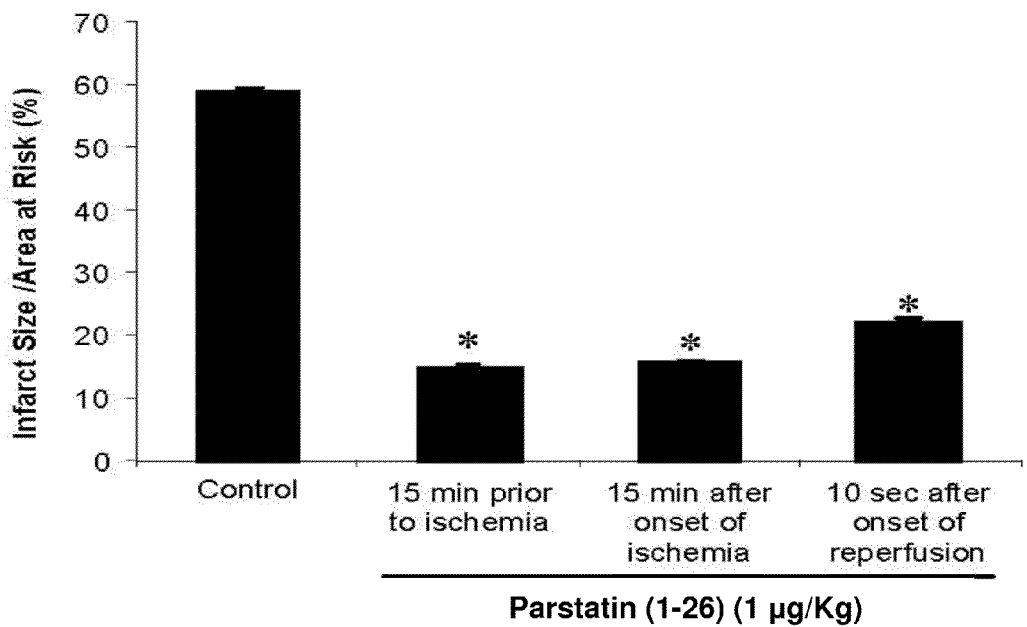

Similar results were also obtained when cell growth was stimulated by VEGF or bFGF with a half-maximal inhibitory concentration of 1 µM parstatin. Mouse parstatin was less effective inhibiting cell proliferation with a half-maximal concentration at 20 µM, whereas scrambled parstatin and short parstatin were without effect (FIG. 4B). These data demonstrate that parstatin decreases the rate of endothelial cell proliferation both within and across species.

Example 7

Parstatin (1-41) Inhibits DNA Synthesis in Endothelial Cells

The ability of parstatin to inhibit DNA synthesis of endothelial cells was assessed in thymidine incorporation assays. HUVEC cells were grown until 60-80% confluent in 24-well plates. Cells were treated with indicated peptides in serum-free medium containing 0.5% BSA, VEGF, bFGF, medium containing 5% FBS, epidermal growth factor (EGF), or heparin-binding EGF (HB-EGF) for 18 hours. All cells were pulsed with 0.5 µCi/ml [3H]-thymidine (ICN Biomedicals Inc., Irvine Calif.) for an additional 6 h. Radioactivity incorporated into DNA was determined with a liquid scintillation counter.

Parstatin (1-41) reduced DNA synthesis in HUVEC cells in a dose-dependent manner, with the inhibitory effect on bFGF- or VEGF-stimulated DNA synthesis being more substantial than that of serum. These data demonstrate more potent activity of parstatin (1-41) on dividing cells rather than quiescent cells.

When DNA synthesis experiments were repeated with cells that were in a quiescent state (100% confluent), the inhibitory effect of parstatin (1-41) was less pronounced (21.6%±7.4 inhibition by 10 µM parstatin in 5% FBS versus 47.3±6.1 on fast-growing cells), indicating a more substantial inhibitory effect for parstatin (1-41) on stimulated endothelial cells.

The continuous presence of parstatin in cell culture was not necessary, since DNA synthesis inhibition was also evident after short exposure of cells to parstatin. Even at the earlier time studied of 30 min exposure, the inhibition of VEGF-induced DNA synthesis was 70% of the maximum (exposure for 24 h) and did not increase further after 1 h exposure to parstatin. These data demonstrate that a single dose of parstatin can have a sustained effect.

As in cell proliferation experiments, mouse parstatin exhibited a significant, but less effective inhibitory effect. Scrambled parstatin and short parstatin (24-41) did not cause any significant effect demonstrating specificity of the parstatin peptides as anti-angiogenic agents.

Example 8

Parstatin (1-41) Inhibits Signaling Through the Map Kinase Pathway

The MAPK (Erk1/2, p42/44) cascade mediates mitogenesis. Cell cycle progression has been shown to depend on sustained activation of the Erk signal transduction pathway. HUVEC cells were cultured in 35 mm tissue culture dishes. After reaching 80% confluency, cells were growth factor-starved and subsequently stimulated for 10 min with vehicle or indicated agents. In combination experiments, cells were pretreated with parstatin or other peptides for 10 to 60 min.

Attached cells were lysed with Laenmli sample buffer, resolved in 10% SDS-PAGE, and transferred to nitrocellulose membranes. Membranes were incubated with primary antibodies against phospho p42/44 mitogen-activated protein kinases (p-Erk1/2, New England Biolabs, UK) and p42/44 Erk1/2 (t-Erk1/2, New England Biolabs, UK). Membranes were then probed with horseradish peroxidase-conjugated secondary antibodies, and proteins were visualized by chemiluminescent detection.

Pretreatment of endothelial cells with parstatin (1-41) for 1 h inhibited the activation of Erk1/2 stimulated either by FBS, bFGF, or VEGF. The inhibitory effect was concentration-dependent. Parstatin essentially blocked the bFGF-induced Erk1/2 phosphorylation levels from a concentration of 3 µM parstatin (1-41). This inhibitory effect was observed at the shortest exposure times. For example, at 10 min, the inhibition of Erk1/2 activation was about 50% of the maximum, indicating a time-dependent effect of parstatin (1-41).

The blockage of Erk1/2 phosphorylation by parstatin (1-41) was found to be almost completely reversible. HUVEC cells exposed to human parstatin (1-41) for 1 h, then washed free of parstatin, and subsequently incubated for further 1 to 3 hours in fresh medium, regained the ability to respond in bFGF and to stimulate the phosphorylation of Erk1/2. As expected, scrambled parstatin did not alter the Erk1/2 activation and mouse parstatin (1-41) had a less pronounced effect as compared to human parstatin at similar concentrations.

Interestingly, the growth inhibitory effect of parstatin (1-41) was specific for bFGF or VEGF, since parstatin did not have any effect on EGF- or HB-EGF-induced DNA synthesis and Erk1/2 activation. These results may provide insight to the mechanism of action of parstatin in the inhibition of cell proliferation and migration.

Example 9

Parstatin (1-41) Inhibits Growth of Endothelial Cells is Associated and Induction of Apoptosis as Demonstrated by Flow Cytometry Flow-cytometric cell cycle analysis was performed to determine whether the inhibitory effect of parstatin on cell growth was a reflection of cytostatic or cytotoxic effects due to cell cycle arrest and apoptosis. HUVEC cells grown in 100 mm tissue culture plates to approximately 80% confluence, were treated in the absence or in the presence of parstatin for 24 h in serum-free medium containing either 0.5% BSA or bFGF.

Attached cells were collected by trypsinization, pooled with suspended cells, washed, and fixed. Fixed cells were then stained with propidium iodide (50 µg/ml, Sigma-Aldrich, St. Louis, Mo.) for 20 min at 4° C. in the dark. Flow cytometry was performed on a FACS flow cytometer (EPICS XL-MCL; Coulter). The propidium iodide-stained cell population in sub-G0/G1, G1, S, and G2/M phases were represented by distinct and quantified peaks in the fluorescence histograms obtained using the WinMDI logical program.

Human parstatin (1-41) increased the subG0/G1 cell fraction, which represents the percentage of apoptotic cells. In addition, parstatin (1-41) increased the cell fraction in G0/G1 phase, indicating that it induced endothelial cell cycle arrest. In agreement with results obtained in growth experiments, parstatin (1-41) reduced the percentages of cells in S and G2/M phases. Similar results were obtained when endothelial cells were stimulated by growth factors, such as bFGF. These data demonstrate an inhibition of cell cycle progression by various angiogenic agonists.

Example 10

Parstatin (1-41) Inhibits Growth of Endothelial Cells, which is Associated with the Induction of Apoptosis, as Demonstrated by Cell Staining The role of parstatin in endothelial cell apoptosis was further explored using the Annexin V/propidium iodide based assay (Annexin V-FITC assay kit, BD Biosciences® PharMingen, Belgium), which is a valuable and very sensitive technique to detect apoptosis. Endothelial cells were grown until approximately 80% confluent. Cells were then treated in the absence or in the presence of human parstatin (1-41) for 24 h in serum-free medium containing either 0.5% BSA, VEGF, or bFGF. The broad spectrum caspase inhibitor Z-VAD-FMK (Z-Val-Ala-Asp(OCH$_3$)-Fluoromethylketone) was used alone or in combination with parstatin at a fixed 100 µM concentration. Attached cells were pooled with suspended cells and resuspended in 100 µL of the kit reaction buffer containing propidium iodide and Annexin V-FITC, according to the manufacturer's instructions. Cells were analyzed on a FACS flow cytometer within 1 h after staining. Cells were analyzed for healthy cells (annexin V- and PI-negative), early apoptotic cells (annexin V-positive, PI-negative) and late apoptotic or dead cells (annexin V- and PI-positive).

The results demonstrated that parstatin (1-41) increased the percentages of endothelial cells in early and late apoptotic stages. In parallel, the percentage of healthy/viable cells was equally decreased. Parstatin (1-41) promoted cell apoptosis in all culture conditions used with the effect to be more pronounced in endothelial cells stimulated by bFGF or VEGF. The apoptotic effect of parstatin (1-41) was concentration-dependent and was reversed by caspase inhibitor Z-VAD-FMK, indicating that caspase activation was involved in parstatin-mediated apoptotic cell death.

Example 11

Parstatin (1-41) Inhibits Growth of Endothelial Cells, which is Associated with the Induction of Apoptosis as Demonstrated by Caspase Activation To further support the involvement of caspases in parstatin's (1-41) pro-apoptotic effect, its effect on caspase-3 activation was examined using a commercially available kit (Promega, Madison, Wis.). The colorimetric substrate, Ac-DEVD-p-nitroanilide, is cleaved by caspase-3 to release yellow p-nitroanilide, which was measured by absorbance at 405 nm to detect caspase activation.

HUVEC cells were grown in 60 mm tissue culture plates until approximately 80% confluent. Cells were treated in the absence or in the presence of 0.5% BSA or bFGF for 24 h in serum-free medium. Suspended and adherent cells were collected and lysed. Caspase-3 activity was measured by absorbance at 405 nm.

Human parstatin (1-41) increased the level of caspase-3 activity in a concentration dependent manner. As expected, bFGF alone significantly reduced the activity of caspase-3, while when it was combined with parstatin (1-41) the caspase-3 activity increased dramatically. The combination of parstatin (1-41) with Z-VAD-FMK resulted in blockage of the action of parstatin, suggesting its specificity for caspase-3. In addition, the promoting activity of parstatin (1-41) was observed as early as 3 hours after the exposure of cells to parstatin. Mouse parstatin (1-41) caused a moderate increase in caspase-3 activity and scrambled parstatin was without effect. These results again demonstrate cross-species, sequence specific activity of parstatins.

Example 12

Parstatin (1-41) Inhibits Growth of Endothelial Cells, which is Associated by the Induction of Apoptosis as Demonstrated by PARP Cleavage PARP is activated in response to DNA damage and is implicated in the repair of DNA strand breaks. PARP cleavage by caspases produces 85- and 24-kDa fragments from the full-length 116-kDa protein. This leads to its inactivation and constitutes an early event in apoptosis.

Western blotting for PARP cleavage was performed on cell lysates from HUVEC cells cultured in serum free medium containing BSA for 24 h. The presence of parstatin (1-41) induced PARP cleavage to its signature 85-kDa fragment in a concentration dependent manner. Parstatin (1-41) also increased PARP cleavage in bFGF-stimulated endothelial cells. Together these results suggest that parstatin (1-41) promoted apoptosis in growing endothelial cells and provide strong evidence that the cytotoxicity observed is due to caspase activation.

Example 13

Parstatin (1-41) is a Cell-Penetrating Peptide

Some signal peptides, due to their highly hydrophobic properties, possess the ability to interact with cell membrane lipid bilayers and to penetrate inside the cell (Lin et al, 1995, J Biol Chem, 270: 14255-14258). To investigate if parstatin exerts its cellular effects as a cell-permeable peptide, human parstatin (1-41) and control peptides were conjugated with FITC. To measure the parstatin uptake into the endothelial cells, two methodological approaches were used: flow cytometry and fluorescence microscopy.

HUVEC cells in the exponential growth phase were exposed to various concentrations of parstatin-FITC in serum-free medium containing 0.5% BSA. After incubation times ranging from 1 min to 60 min, cells were washed extensively. Washed cells were incubated for 10 min with trypsin at 37° C. to remove the cell surface-bound parstatin. Suspended cells were subsequently centrifuged, washed, and analyzed on FACS flow cytometer (EPICS XL-MCL; Coulter).

The uptake of parstatin-FITC into cells was assessed by the change of the FITC-positive cell population compared with untreated control cell samples. The fraction of the FITC-positive cell population exposed to parstatin-FITC for 30 min was increased in a dose-dependent manner. In addition, the uptake kinetics of parstatin into endothelial cells suggested a non-saturable, non-receptor mediated uptake. Even at the shortest time of exposure to parstatin studied (1 min) the FITC-positive cell population was 13.4% and reached to a maximal level after 30 min of treatment.

For imaging, endothelial cells were incubated with FITC-labelled parstatin as described above and the distribution of the parstatins was observed with fluorescent microscopy. 4',6-Diamidino-2-phenylindole (DAPI) was used to stain nuclei of all cells. Cell fluorescence was imaged on a Nikon Eclipse TE2000-U microscope. FITC and DAPI were excited using 490-nm and 360-nm filters, respectively. The emission signals were sorted out using 514 and 460 filters for the FITC and DAPI, respectively.

HUVEC cells were treated with 10 μM of parstatin(1-41)-FITC for different time intervals. In control sample, for which no fluorescence was observed, cells were not exposed to parstatin(1-41)-FITC. FITC signal was detected as early as 5 min of cell exposure to parstatin(1-41)-FITC. At this time point, parstatin (1-41) signal was exclusively localized in cell membranes. When endothelial cells were exposed to parstatin (1-41)-FITC for 10 min the FITC signal was detected in cell membranes and in the cytosol. The exposure of cells for 30 min resulted in signal localization only in the cytosol, preferentially around the nucleus.

These data suggest that parstatin (1-41) possesses the ability to interact with cell membranes and enter cells at a rate dependent on the exposure time and the concentration applied. They also suggest that parstatin peptides including the N-terminal sequence may be exceptionally useful and readily taken up in topical or local applications (e.g., intraocular injections for the treatment of retinal angiogenesis). This kinetic profile was in agreement with the initiation of parstatin-mediated biological effects (e.g. the inhibition of bFGF-induced MAPK activation). These data also suggest that cell membrane fluidity and membrane protein mobility were important for parstatin cell penetration, because low temperature or pretreatment of cells with paraformaldehyde prevented parstatin (1-41) peptide uptake. In addition, receptor-mediated uptake did not seem to be involved. An excess of unlabeled peptide, inhibitors of endosomal/lysosomal uptake, and an inhibitor of protein synthesis (cycloheximide) were without effect on peptide uptake. Taken together, these results provide evidence that parstatin (1-41) is a cell-penetrating peptide which exerts its biological effects intracellularly.

Example 14

Parstatin (1-41) Attenuates Myocardial Ischemia-Reperfusion Injury in Rats

Parstatin (1-41) was used in an in vivo rat model of cardiac ischemia and reperfusion, and in an in vitro isolated rat heart model of ischemia-reperfusion injury. Male Sprague Dawley rats at 8 weeks of age were used and treated in compliance with the "Guide for the Care and Use of Laboratory Animals" formulated by the National Research Council (USA), 1996.

For in vivo infarct size studies, rats were anesthetized with pentobarbital sodium (50 mg/Kg) and heparin (1000 IU/Kg) and underwent 30 min of regional ischemia followed by 180 min of reperfusion. Parstatin (1-41) was administered intravenously over 1 min starting 15 min prior to ischemia, 15 min after the onset of ischemia, and 5 min after the onset of reperfusion in separate series of experiments (n=6/group).

To induce ischemia, ligature was positioned around the left main coronary artery and threaded through a plastic snare to permit reversible occlusion of the coronary artery. Coronary occlusion was induced by clamping the snare onto the heart and reperfusion was achieved by releasing the snare. At the end of reperfusion, the coronary artery was re-occluded and the risk zone was delineated by perfusion of 0.5% Evans' blue into the aortic cannula.

Hearts were sectioned and incubated in 1% triphenyltetrazolium chloride in phosphate buffer for 15 min to define white necrotic tissue when fixed in 10% formalin for 24 h. Area at risk (AAR) and infarct-to-risk rations were determined by computerized planimetry using J-Image v.i.6 software (NIH, Bethesda, Mass.). Infarct size was 64±2% of the AAR in the control group. In rats that received parstatin, a concentration-dependant reduction in infarct size was seen, with an optimal dose at 30 μg/Kg. These hearts had an infarct size of 40±5, which is a 37.5% reduction in infarct size compared to the control.

Heart rate and blood pressures were monitored throughout the procedure and there were no significant differences between baseline hemodynamics of the groups. Mean arterial pressure decreased during ischemia and reperfusion in all groups but there was no significant difference between groups. In addition, rats were treated with an IV bolus of 30 μg/Kg of parstatin 15 min after the onset of ischemia or 5 minutes after initiation of reperfusion. Parstatin (1041) was able to reduce infarct size when administered during ischemia by 25% and at reperfusion by 21% when compared to control. These data demonstrate that parstatin peptides are useful for both prophylaxis and treatment of ischemia/reperfusion injury.

Example 15

Parstatin (1-41) Attenuates Myocardial Ischemia-Reperfusion Injury in Excised Hearts For in vitro studies, excised hearts were retrogradely perfused through the aorta with a modified Krebs buffer. Coronary flow rate was determined by timed collection of the coronary effluent. A saline-filled latex balloon connected to a pressure transducer was inserted into the left vertical (LV), and baseline end-diastolic pressure was set at 5-10 mmHg Heart rate, LV end-diastolic pressure and LV developed pressures (LVDP) were recorded continuously. The measurements for post-ischemic recovery of LVDP used for comparison were taken at 180 min of reperfusion. After stabilization for 15-20 min, the hearts (n=6/group) were subjected to 30 min of regional ischemia, followed by 180 min of reperfusion.

Different concentrations of parstatin (1-41) were perfused 15 min prior to coronary occlusion until occlusion. L-NMMA, a specific inhibitor of nitric oxide synthase was perfused 15 min prior to the addition of parstatin. Control hearts had an infarct size of 51±3% of the AAR, whereas continuous administration of parstatin (1-41) resulted in a concentration-dependent reduction of infarct size. Parstatin (1-41) at 1 μM led to the largest reduction in infarct size (18.3±3%), a 64% decrease. At this concentration, parstatin increased recovery of LVDP by a significant extent (76±5% versus 59±5% of control). There were no differences in hemodynamics at any points measured between control and parstatin (1-41)-treated groups. In addition, blockage of nitric oxide synthase by L-NMMA (100 μM) abolished the effect of parstatin, suggesting a role of nitric oxide pathway in the cardioprotective action of parstatin. Again, these data demonstrate the utility of parstatin peptides as both cardioprotective and therapeutic agents across species.

Example 16

Parstatin Peptides Suppress Choriodal Neovascularization in Mice

Parstatin (1-41) and a hydrophobic parstatin (1-26) fragment were used in an in vivo mouse model of choriodal neovascularization. In particular, laser photocoagulation-induced rupture of Bruch's membrane was used to generate choriodal neovascularization as a preclinical disease model for age-related macular degeneration. Pathogen-free C57BL/6J (4-5 week-old) mice were treated in accordance with the Association for Research in Vision and Opthalmology Statement for the Use of Animals in Ophthalmic and Vision Research and the guidelines of the Animal Care and Use Committee at local University Medical School.

Mice were anesthetized with ketamine hydrochloride (100 mg/kg body weight) and the pupils were dilated with 1% tropicamide. Laser photocoagulation (75 nm spot size, 0.1 sec duration, 120 mW) was performed in the 9, 12, and 3 o'clock positions of the posterior pole of the retina with the slit lamp delivery system of an Oculight GL diode laser (Iridex, Mountain View, Calif.) and a handheld cover slip as a contact lens to view the retina. Production of a bubble at the time of laser, which indicates rupture of Bruch's membrane, is an important factor in obtaining choriodal neovascularization. Therefore, only burns in which a bubble was produced were included in the study. Two weeks after rupture of Bruch's membrane, anesthetized mice were perfused with 50 mg/ml fluorescein-labelled dextran (average molecular weight, 2×106). The eyes were then dissected and fixed in 10% Formalin for 3 hours and choriodal flat mounts were examined by fluorescence microscopy. Image-Pro Plus software was used to measure the total area of choriodal neovascularization at each rupture site.

Intraocular injections of parstatin peptides were performed with a Harvard pump microinjection apparatus and pulled glass micropipets. Under a dissecting microscope, the sharpened tip of a micropipette was passed through the sclera just behind the limbus into the vitreous cavity. Intravitreal injections of 1 μl solutions of 0.5, 1, 3, 10, or 30 μg parstatin (1-41) in phosphate buffered saline (PBS) or PBS alone were administered. Also, intravitreal injections of 1 μl solutions of 10 μg parstatin (1-26) in dimethyl sulphoxide (DMSO) or DMSO alone were administered Intravitreal injections were administered immediately after laser treatment and 7 days after laser treatment. Choriodal neovascularization was assessed 14 days after laser treatment.

As shown in FIGS. 1A, B and C, parstatin (1-41) was a very potent antiangiogenic agent. Mice that received intraocular injections of parstatin (1-41) had areas of neovascularization that were much smaller than those seen in control mice treated with vehicle (PBS). Measurements of the area of choriodal neovascularization by image analysis confirmed that there was significantly less neovascularization in eyes treated with parstatin (1-41) compared to control mice (FIG. 1D). The inhibitory effect of parstatin was dose-dependent and the maximum inhibition of choriodal neovascularization was demonstrated with the 10 μg dose which showed a 73% inhibition. This is comparable to the best known treatments for suppressing choriodal neovascularization, such as anti-VEGF, anti-VEGFR2 or anti-PlGF treatment. The dose of 30 μg did not provide additional benefit, but it was well tolerated by adult mice. Mice treated with scrambled parstatin had choriodal neovascularization similar to that obtained in control mice treated with PBS (FIG. 1D). Mice treated with parstatin (1-26) had choriodal neovascularization significantly inhibited by 62% compared to control mice treated with DMSO (FIG. 1E).

Example 17

Parstatin (1-41) Peptide Suppresses Retinal Neovascularization in Mice

Parstatin (1-41) was used in an in vivo mouse model of retinal neovascularization. In particular, oxygen-induced retinopathy was used to generate retinal neovascularization as a preclinical disease model for retinopathy of prematurity and other retinal neovascular diseases such as diabetic retinopathy. In this model, exposing newborn mice to hyperoxia prompts regression or delay of retinal vascular development, followed by abnormal angiogenesis after their return to normal oxygen levels. Mainly, this model mirrors the events that occur during retinopathy of prematurity, when infants are removed from oxygen-rich incubators, a condition involving pathological neovascularization that can affect premature infants and result in permanent visual loss. In recent years, the use of this model has been extended to the general study of ischemic vasculopathies, such us diabetic retinopathy, and related antiangiogenic interventions, and it is now used extensively in both basic and applied research environments.

Pathogen-free C57BL/6 mice were treated in accordance with the Association for Research in Vision and Opthalmology Statement for the Use of Animals in Ophthalmic and Vision Research and the guidelines of the Animal Care and Use Committee at local University Medical School. Litters of 7-day old (P7) mice were exposed to an atmosphere of 75% oxygen in an airtight incubator for 5 days (P12), after which they were returned to room air for 5 days (P17). For quantification of oxygen-induced retinal neovascularization mice on P17 were given an intraocular injection of 1 μl of rat anti-mouse platelet endothelial cell adhesion molecule-1 (PECAM-1) antibody under a dissecting microscope with a Harvard pump microinjection apparatus and pulled glass micropipets. Mice were euthanized 12 hours after injection and eyes were fixed in PBS-buffered formalin for 5 hours. Retinas were dissected, washed and incubated with goat anti-rat polyclonal antibody conjugated with Alexa 488 for 45 min Retinal flat mounts were prepared and assessed with a fluorescence microscope using imaging software. Intravitreal injections of 1 μl solutions of 0.5, 1, 3, 10, or 30 μg parstatin in PBS or PBS alone were administered on P12 (immediately after the mice are removed from hyperoxic conditions) and P15.

Figure 2:
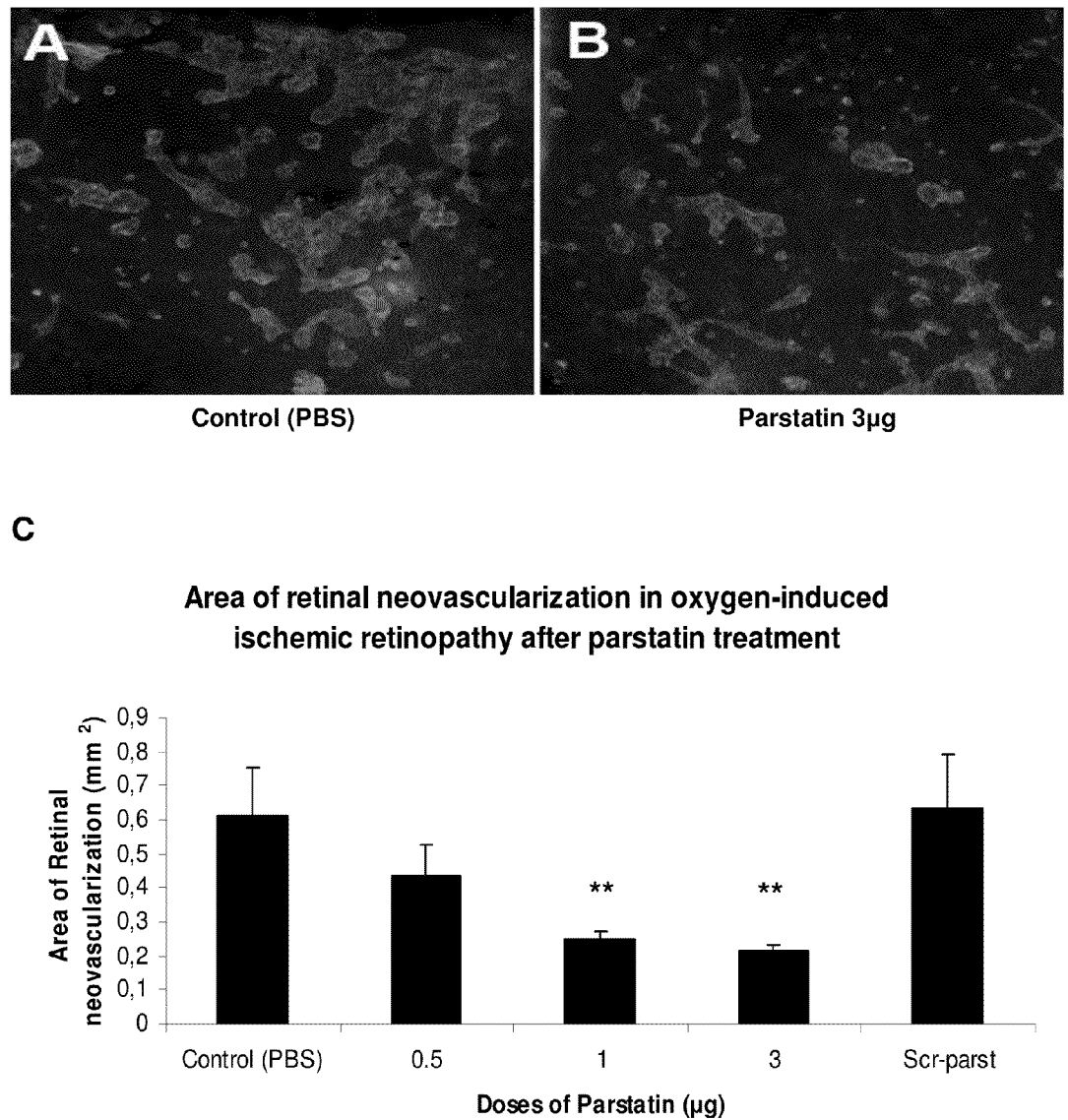

As shown in FIGS. 2A and B, mice that received intraocular injections of parstatin (1-41) had areas of retinal neovascularization that were much smaller than those seen in control mice treated with vehicle (PBS). Measurements of the area of retinal neovascularization by image analysis confirmed that there was significantly less neovascularization in eyes treated with parstatin (1-41) compared to control mice (FIG. 2C). The inhibitory effect of parstatin (1-41) was dose-dependent and at doses of 1 and 3 μg resulted in significant inhibition of retinal neovascularization. At a dose of 3 μg, parstatin (1-41) suppressed neovascularization by 64%. Doses of 10 and 30 μg were not well tolerated when administered to P12-P15 mice. Retinal adherence made the retinas virtually impossible to retrieve. There was also adherence of the eyelids and occasional cataract formation with these doses. Mice treated with scrambled parstatin had retinal neovascularization similar to that obtained in control mice treated with PBS (FIG. 2C) and did not exhibit any effect even at dose of 100 µg.

Example 18

Parstatin (1-41) Peptide Suppresses Corneal Neovascularization in Rats

Parstatin (1-41) was used in an in vivo rat model of corneal neovascularization. In particular, chemical burn-induced corneal trauma was used to generate corneal neovascularization as a preclinical disease model simulating a plethora of corneal diseases associated with abnormal formation of new blood vessels. The cornea is normally an avascular tissue that can be stimulated to undergo pathological neoangiogenesis in response to mechanical or chemical injuries, pterygium, herpetic keratitis, etc. In this model, an inflammatory response is considered an important prerequisite for neovascularization. This model is widely accepted and is one of the most extensively studied models, which provides an in vivo environment to study this complex process with convenient access to the corneal tissue and the highly visible developing vasculature.

Pathogen-free male Sprague-Dawley rats (250-300 gr) were treated in accordance with the Association for Research in Vision and Opthalmology Statement for the Use of Animals in Ophthalmic and Vision Research and the guidelines of the Animal Care and Use Committee at local University Medical School. Rats were anesthetized with an intramuscular injection of ketamine (25 mg/Kg) and xylazine hydrochloride (10 mg/Kg). The right eye of each animal was washed with saline, sterilized with povidone 5% and cauterized by pressing an applicator stick coated with 75% silver nitrate and 25% potassium nitrate to the center of the cornea for 4 second to stimulate angiogenesis. The burn area and conjunctival sac were irrigated with 15 ml saline for 15 seconds. The injured eyes then received topical antibiotics.

Immediately after the burns, rats were randomly divided into groups and each injured eye was double subconjunctivally injected with 2×20 µl solutions of 50, 75, 100, 200 µg/20 µl parstatin (1-41) in PBS or PBS alone. Injections were performed in the 12, and 6 o'clock positions of the anterior pole of the cornea. Seven days later, each eye underwent slit-lamp examination and serial photographs of the cornea were taken. The corneal neovascularization was assessed using image analysis software (Image Pro Plus™, Media Cybernetics, Bethesda, Md., USA). The new corneal vessels were quantified by calculating the wedge-shaped area of vessel growth with the following formula: A=C/12×3.1416 [r2−(r−1)2], where A is the area, C is time (in hours), 1 is the radius from the center to the border of vessel growth, and r is the radius of the cornea. The degree of neovascularization was compared between the groups using the ration of the area of neovascularization to the whole corneal area.

The rats were killed on day 7. The eyeballs were removed and fixed in formalin. The corneal specimens were embedded in paraffin, cross-sectioned and stained with hematoxylin and eosin and blood vessels in the corneal section were counted.

Figure 3:
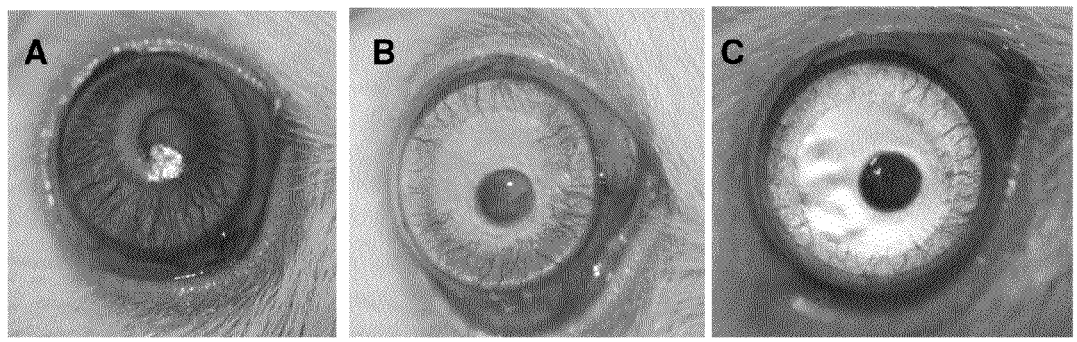
Figure 3:
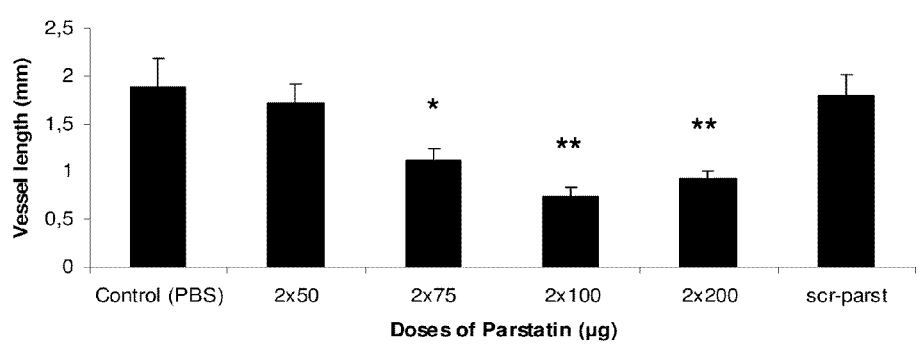
Figure 3:
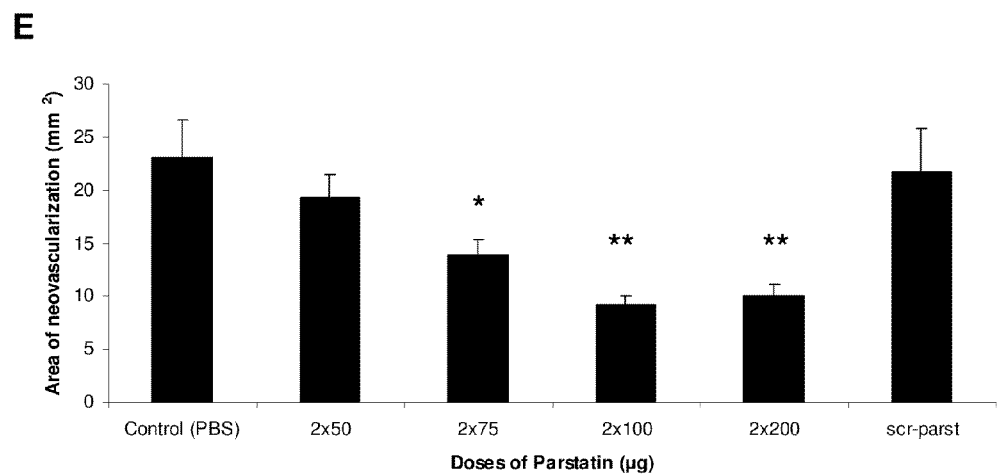

As shown in FIGS. 3A, B, and C, rats that received subconjunctival injections of parstatin (1-41) had areas of corneal neovascularization that were much smaller than those seen in control mice treated with vehicle (PBS). Measurements of the length and the area of corneal neovascularization by image analysis confirmed that there was significantly less neovascularization in eyes treated with parstatin compared to control mice (FIGS. 3D and E). The inhibitory effect of parstatin was dose-dependent and at doses ranging from 2×75 µg to 2×200 µg resulted in significant inhibition of corneal neovascularization. At a dose of 2×100 µg, parstatin suppressed neovascularization by 60% ($p<0.01$). The dose of 2×200 µg did not provide additional benefit, but it was well tolerated by rats. Rats treated with scrambled parstatin (2×100 µg) had corneal neovascularization similar to that obtained in control rats treated with PBS (FIGS. 3D and E).

Example 19

Hydrophobic Parstatin (1-26) Fragment Attenuates Myocardial Ischemia-Reperfusion Injury in Rats The protective activity of an N-terminal hydrophobic parstatin (1-26) fragment was assayed in an in vivo rat model of myocardial ischemia-reperfusion injury. Male Sprague Dawley rats at 8 weeks of age were used and treated in compliance with the "Guide for the Care and Use of Laboratory Animals" published by the US National Institutes of Health (NIH Publication NO. 85-23, revised 1996).

For in vivo infarct size/ischemia-reperfusion studies, rats were anesthetized with pentobarbital sodium (50 mg/Kg) and heparin (1000 IU/Kg) and underwent 30 min of regional ischemia followed by 120 min of reperfusion. Human hydrophobic parstatin (1-26) fragment (sequence: MGPRRLLLVAACFSLCGPLLSARTRA, amino acids 1-26 of SEQ ID NO: 1) was administered intravenously over 1 min at one of three time points: 1) starting 15 min prior to ischemia, 2) 15 min after the onset of ischemia, or 3) 10 seconds after the onset of reperfusion in a separate series of experiments (n=6/group).

Ischemia was induced by placement of a ligature around the left main coronary artery which was threaded through a plastic snare to permit reversible occlusion of the coronary artery. Coronary occlusion was induced by clamping the snare onto the heart and reperfusion was achieved by releasing the snare. At the end of reperfusion, the coronary artery was re-occluded and the risk zone was delineated by perfusion 0.5% Evans' blue into the aortic cannula.

Hearts were sectioned and incubated in 1% triphenyltetrazolium chloride in phosphate buffer for 15 min to define white necrotic tissue when fixed in 10% formalin for 24 h. Area at risk (AAR) and infarct-to-risk rations were determined by computerized planimetry using J-Image v.i.6 software (NIH, Bethesda, Mass.).

A dose response analysis (0.01-10 µg/Kg) of hydrophobic parstatin (1-26) fragment was performed to determine its optimal protective dose and compare it to the optimal protective dose of full parstatin (1-41) peptide (10 µg/Kg). The molecular weight of parstatin (1-26) is about 63% of the molecular weight of full length parstatin (1-41). The principal endpoint of these studies was infarct size expressed as a percentage of the area at risk.

As shown in FIG. 4A, significant and dose-dependent changes in infarct size were detected with the 0.01, 0.1 and 1 µg/Kg doses of hydrophobic parstatin (1-26) fragment. Infarct size was 58±1% of the area at risk in the control group. The cardioprotective effects of the hydrophobic parstatin (1-26) fragment reached a plateau at 10 µg/Kg. At this dose of hydrophobic parstatin (1-26) fragment, infarct size was 13±1% of the area at risk, a 78% reduction in infarct size. Pre-ischemic treatment with full parstatin (1-41) reduced infarct size to 39±2% area at risk; a 31% reduction (FIG. 4A).

Heart rate and blood pressures were monitored throughout the procedure and there were no significant differences between baseline hemodynamics between groups. Mean arterial pressure decreased during ischemia and reperfusion in all groups but there was no significant difference between groups. In addition, rats were treated with an IV bolus of 1 µg/Kg of the hydrophobic parstatin (1-26) fragment 15 min after the onset of ischemia or 10 seconds after initiation of reperfusion. The hydrophobic parstatin (1-26) fragment was able to reduce infarct size when administered during ischemia by 73% and at reperfusion by 62% when compared to control (FIG. 4B).

These data demonstrate that the hydrophobic parstatin (1-26) fragment is more potent than the full parstatin peptide and is useful for both prophylaxis and treatment of myocardial ischemia/reperfusion injury.

Example 20

The Cardioprotective Properties of the Hydrophobic Parstatin (1-26) Fragment are Largely Dependant Upon a $G_i$ Protein Mediated Pathway and Involve the Activation of Akt, Nitric Oxide Synthase (NOS), Soluble Guanylyl Cyclase (sGC) and $K^+$ATP Channels Preconditioning refers to the phenomenon by which the heart is put into a state of self-preservation. This is of therapeutic importance considering the high mortality and morbidity of ischemic heart diseases. Preconditioning is triggered by either brief cycles of ischemia or by exogenous agents which typically activate $G_i$ protein coupled surface receptors to set off a complex pathway which ultimately results in cell survival (Schultz et al., 1998, Am J. Physiol., 275: H495-H500). $G_i$ proteins are able to activate components of the reperfusion injury salvage kinase pathway including PI3K/Akt and ERK1/2 (Hausenloy and Yellon, 2006, Cardiovasc Res., 70: 240-253). Akt is pivotal in the reperfusion injury salvage kinase pathway either by inactivation of the apoptotic pathway, for instance preventing the activation and translocation of BAX to the mitochondrial membrane or by activating endothelial NOS to increase production of NO (Cantley, 2002, Science, 296: 1655-1657). Nitric oxide subsequently targets sGC which results in the conversion of guanosine-5'-triphophate to the intracellular second messenger cyclic guanosine monophosphate (cGMP). $K^+$ATP channels are opened in a cGMP-dependent manner (Oldenburg et al., 2004, Am J Physiol Heart Circ Physiol., 286: H468-H476; Qin et al., 2004, Am J Physiol Heart Circ Physiol., 287: H712-H718). Activation of sarcolemmal $K^+$ATP channels shortens action membrane potential duration and decreases intracellular $Ca^{2+}$ loading (Budas et al., 2004, FASEB J., 18: 1046-1048; Budas et al., 2006, FASEB J., 20: 2556-2558) and mitochondrial $K^+$ATP channel opening attenuates mitochondrial calcium accumulation, prevents $Ca^{2+}$-promoted oxidative stress, and maintains mitochondrial membrane integrity. Therefore, PI3K/Akt signaling may recruit multiple cardioprotective pathways to reduce myocardial damage after ischemia and reperfusion.

Figure 5:
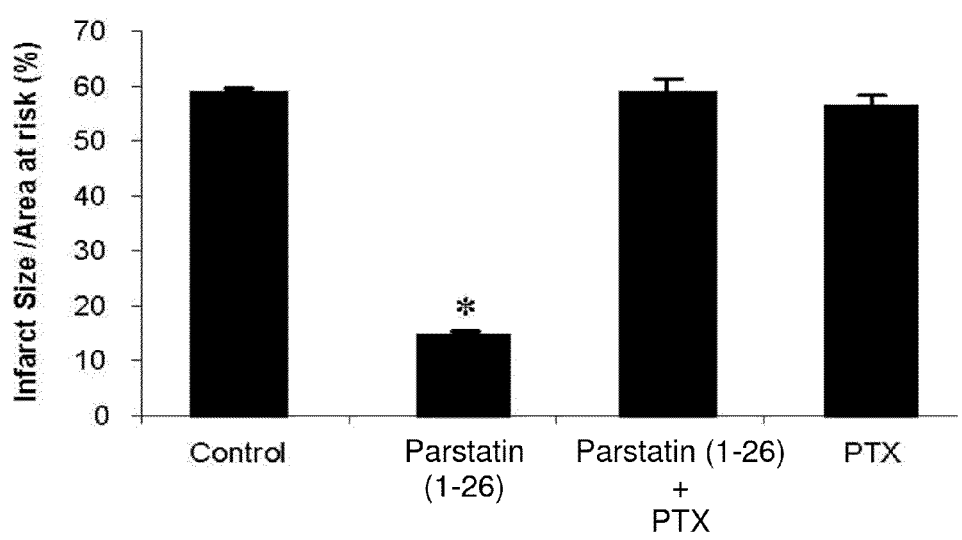
FIG. 5. The cardioprotective effects of hydrophobic parstatin fragment 1-26 are dependent on Gi proteins Inhibition of Gi protein activation by pertussis toxin (PTX) completely abolished the cardioprotective effects of hydrophobic parstatin fragment 1-26 [parstatin (1-26)]. Pertussis toxin was injected 48 hours prior to ischemia. The rats were treated with hydrophobic parstatin fragment 1-26 (1 µg/kg) 15 min prior to ischemia and then subjected to 30 min ischemia and 120 min reperfusion. Control rats received vehicle only. Infarct size expressed as percentage of area at risk. Data are means±SE, n=6 rats/group, *P<0.01.

To determine a possible mechanism for the observed cardioprotective effects of parstatin peptides, rats were treated with pertussis toxin (25 µg/Kg, a potent inhibitor of $G_i$ proteins) 48 hours prior to ischemia. The rats were then treated with or without hydrophobic parstatin (1-26) fragment (1 µg/Kg) 15 min prior the ischemia. Rats were then subject to 30 min ischemia and 120 min reperfusion. As shown in the FIG. 5, in the presence of pertussis toxin the hydrophobic parstatin (1-26) fragment was unable to reduce infarct size after ischemia-reperfusion injury.

Figure 6:
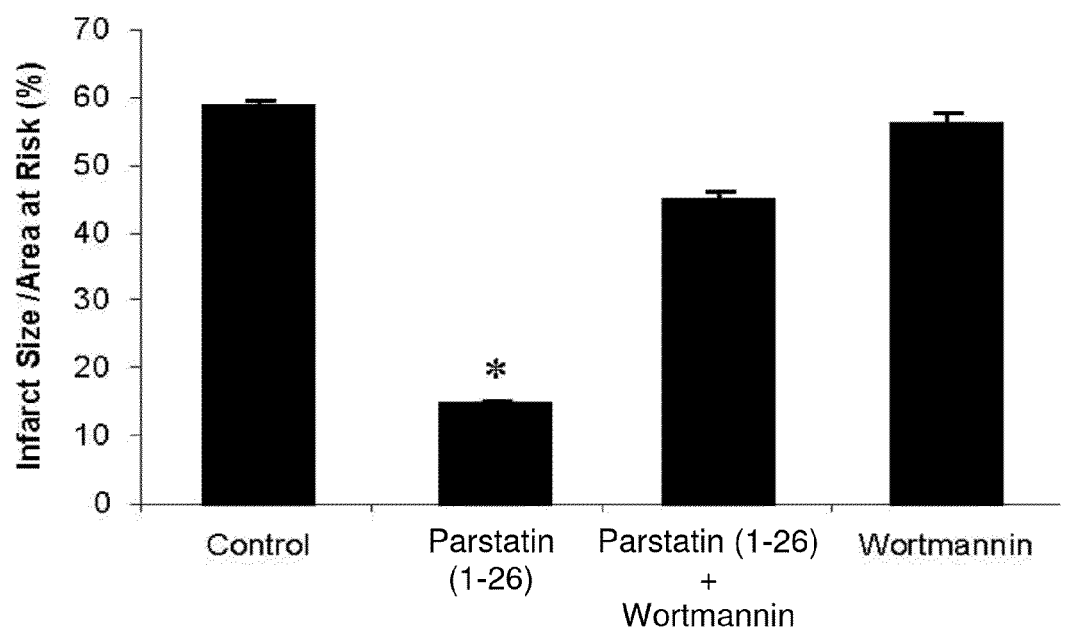
FIG. 6. The cardioprotective effects of hydrophobic parstatin fragment 1-26 are dependent on PI3K/Akt activation. A, Inhibition of PI3K/Akt with wortmannin negates the cardioprotective effects of hydrophobic parstatin fragment 1-26 [parstatin (1-26)]. Wortmannin (15 µg/kg) was injected 30 min prior to ischemia. The rats were treated with hydrophobic parstatin fragment 1-26 (1 µg/kg) 15 min prior to ischemia and then subjected to 30 min ischemia and 120 min reperfusion. Control rats received vehicle only. Infarct size is expressed as percentage of area at risk. Data are means±SE, n=6 rats/group, *P<0.01. B, Hydrophobic parstatin fragment 1-26 increased the activation of Akt after 5 min of reperfusion. Rats were treated with hydrophobic parstatin fragment 1-26 [parstatin (1-26), 1 µg/kg] with or without wortmannin (15 µg/kg) and subjected to 30 min regional ischemia and 5 min reperfusion before the free wall of the left ventricle was harvested for protein extraction. The phosphorylation levels of Akt were detected by Western Blot analysis. Sham rats did not undergo ischemia and control rats received vehicle only. GAPDH was used as a protein loading control, n=3 hearts/group.
Figure 6:
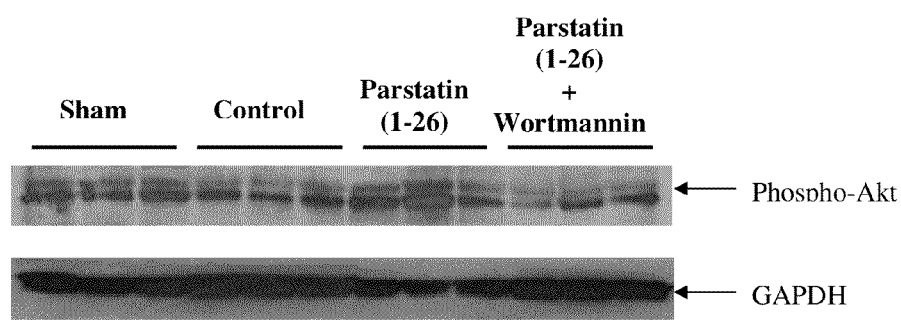

To determine whether the cardioprotective effect of hydrophobic parstatin (1-26) fragment is mediated through the PI3K/Akt pathway, rats were treated with wortmannin (15 µg/Kg, a potent and specific PI3K inhibitor) alone or in combination with hydrophobic parstatin fragment 1-26 (1 µg/Kg). As shown in the FIG. 6A, wortmannin abrogated the cardioprotective effects of hydrophobic parstatin (1-26) fragment. In addition, the left ventricular free wall tissue was homogenized and immunoblot analysis was performed using an anti-phospho-Akt (Ser473) primary antibody (Cell Signaling Technology, Danvers, Mass.). Pre-ischemic treatment of hydrophobic parstatin fragment 1-26 increased phosphorylation of Akt/Ser473 after 5 min reperfusion when compared to hearts from control rats (FIG. 6B). Co-treatment with wortmannin blocked hydrophobic parstastin (1-26) fragment-mediated Akt phosphorylation.

Figure 7:
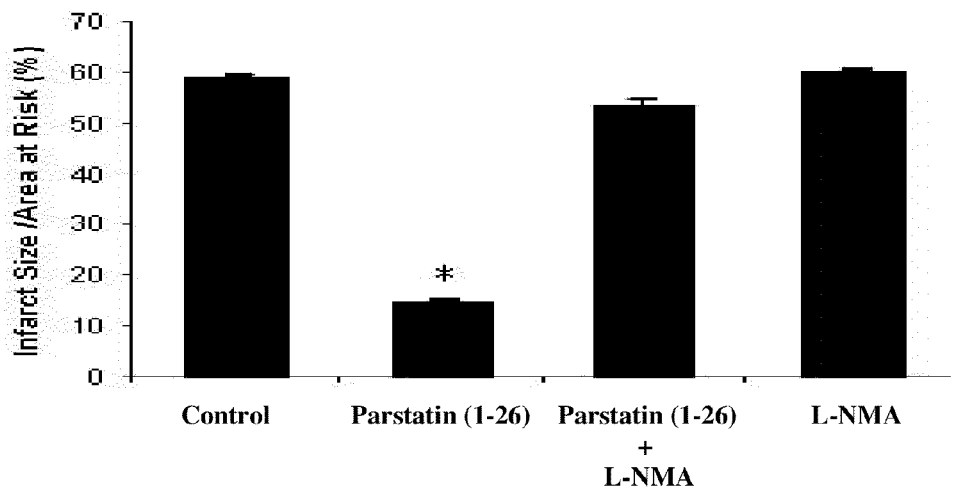
FIG. 7. The cardioprotective effects of hydrophobic parstatin fragment 1-26 are dependent on nitric oxide synthase activation and nitric oxide production. A, Inhibition of nitric oxide synthase with L-NMA abolished the cardioprotective effects of hydrophobic parstatin fragment 1-26 [parstatin (1-26)]. L-NMA (15 mg/kg) was injected 30 min prior to ischemia. The rats were treated with hydrophobic parstatin fragment 1-26 (1 µg/kg) 15 min prior to ischemia and then subjected to 30 min ischemia and 120 min reperfusion. Control rats received vehicle only. Infarct size is expressed as percentage of area at risk. Data are means±SE, n=6 rats/group, *P<0.01. B, Hydrophobic parstatin fragment 1-26 increased the activation of endothelial nitric oxide synthase (eNOS) after 5 min of reperfusion. Rats were treated with hydrophobic parstatin fragment 1-26 [parstatin (1-26), 1 µg/kg] with or without wortmannin (15 µg/kg) and subjected to 30 min regional ischemia and 5 min reperfusion before the free wall of the left ventricle was harvested for protein extraction. The phosphorylation levels of eNOS were detected by Western Blot analysis. Sham rats did not undergo ischemia and control rats received vehicle only. GAPDH was used as a protein loading control, n=3 hearts/group. C, Pre-ischemic treatment with hydrophobic parstatin fragment 1-26 (1 µg/kg) increased the myocardial nitric oxide content. Total nitrite and nitrates were measured in ischemic and non-ischemic myocardium. The rats were treated with hydrophobic parstatin fragment 1-26 (1 µg/kg) 15 min prior to ischemia and then subjected to 30 min ischemia and 120 min reperfusion. Control rats received vehicle only. Data are means±SE, n=6 rats/group, *P<0.01.
Figure 7:
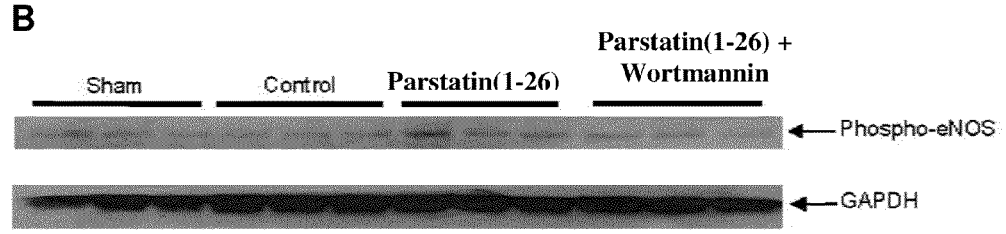
Figure 7:
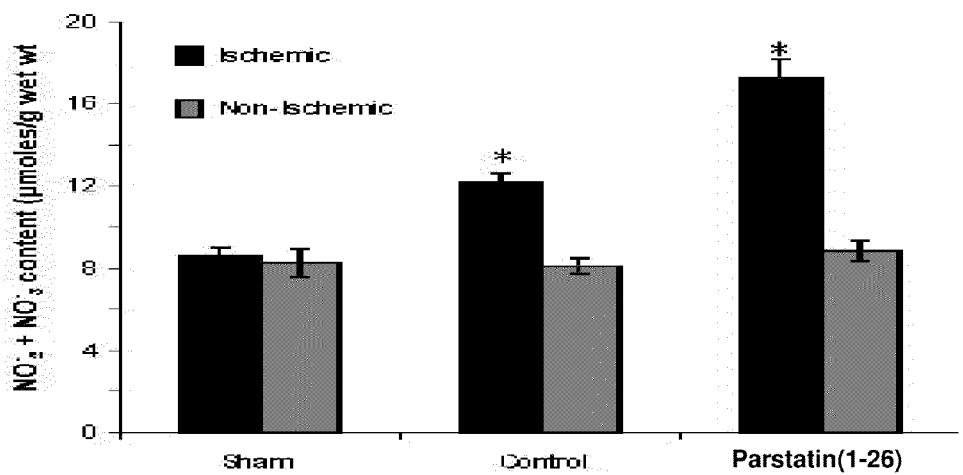

To determine whether the hydrophobic parstatin (1-26) fragment protects the heart by a mechanism involving nitric oxide synthase (NOS), rats were treated with L-NMA (15 µg/Kg, a general NOS inhibitor, with or without the hydrophobic parstatin (1-26) fragment (1 µg/Kg) prior to ischemia. As shown in FIG. 7A, L-NMA abolished the infarct sparing effect of hydrophobic parstatin (1-26) fragment, while L-NMA alone was without effect. The role of the hydrophobic parstatin (1-26) fragment in endothelial NOS activation was further evaluated by measuring the phosphorylation of Ser1177. In these experiments, the left ventricular free wall tissue was homogenized and immunoblot analysis was performed using an anti-phospho-endothelial NOS (Ser1177) primary antibody (Cell Signaling Technology, Danvers, Mass.). Hydrophobic parstatin fragment 1-26 treatment increased endothelial NOS phosphorylation after 5 min reperfusion (FIG. 7B). Wortmannin blocked hydrophobic parstatin fragment 1-26-stimulated Ser1177 phosphorylation, suggesting that Akt participates in Ser1177-stimulated endothelial NOS activation (FIG. 7B). In addition, nitrite and nitrate content, a marker of endothelial NOS activity, was measured from both ischemic and non-ischemic tissues. Ischemia and 120 min reperfusion caused an increase in the production of NO in the ischemic tissue from the control group when compared to the sham group (FIG. 7C). However, no difference in NO content was observed in non-ischemic tissue in the control group when compared to sham rats. Pre-ischemic treatment with the hydrophobic parstatin fragment 1-26 further increased NO content in the ischemic tissue by an additional 1.4-fold over control values and 2.0-fold over sham treated values. No differences in NO levels were detected in non-ischemic tissue receiving the treatment compared to control and sham rats (FIG. 7C).

Figure 8:
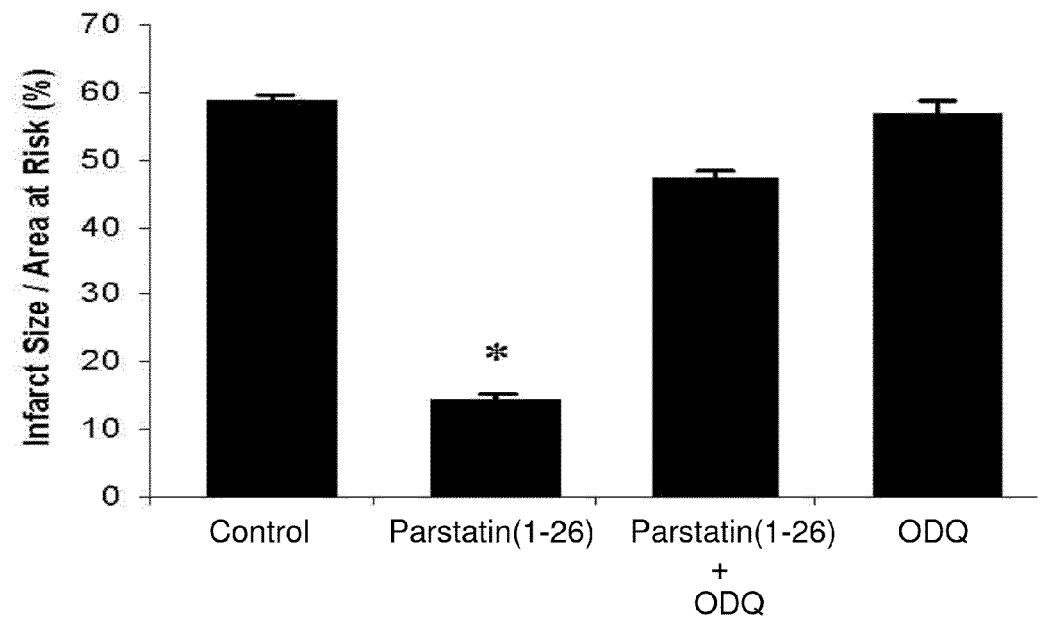
FIG. 8. The cardioprotective effects of hydrophobic parstatin fragment 1-26 are dependent on soluble guanylyl cyclase activation and increased GMP production. A, Inhibition of soluble guanylyl cyclase with ODQ abolished the cardioprotective effects of hydrophobic parstatin fragment 1-26 [parstatin (1-26)]. ODQ (1 mg/kg) was injected 30 min prior to ischemia. The rats were treated with hydrophobic parstatin fragment 1-26 (1 µg/kg) 15 min prior to ischemia and then subjected to 30 min ischemia and 120 min reperfusion. Control rats received vehicle only. Infarct size expressed as percentage of area at risk. Data are means±SE, n=6 rats/group, *P<0.01. B, Pre-ischemic treatment with hydrophobic parstatin fragment 1-26 (1 µg/kg) increased the myocardial cGMP content. Total cGMP was measured in ischemic and non-ischemic myocardium. The rats were treated with hydrophobic parstatin fragment 1-26 (1 µg/kg) 15 min prior to ischemia and then subjected to 30 min ischemia and 120 min reperfusion. Control rats received vehicle only. Data are means±SE, n=6 rats/group, *P<0.01.
Figure 8:
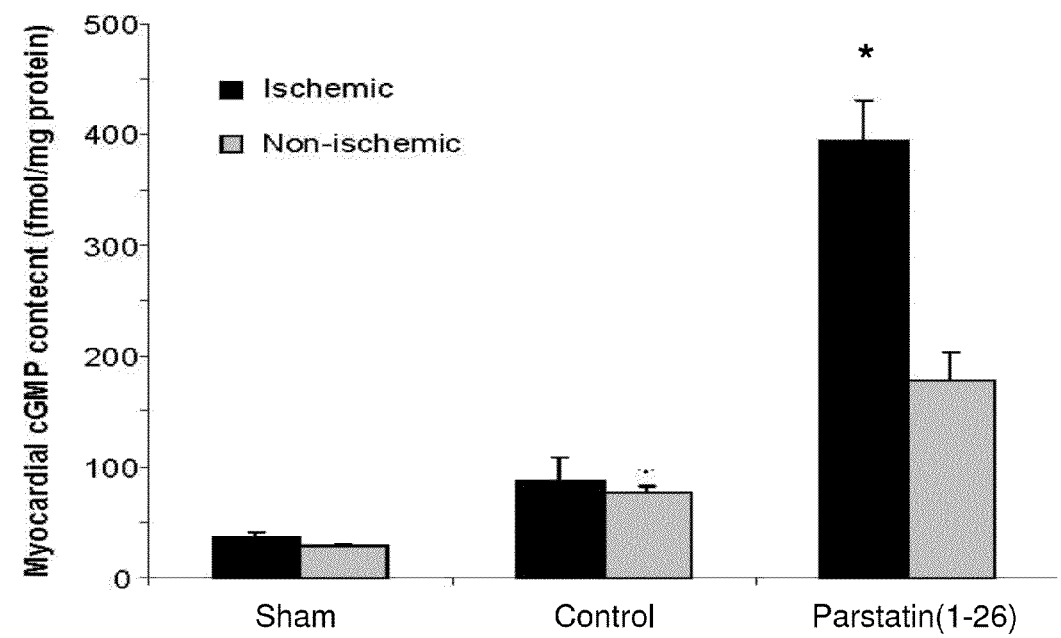

To determine whether the hydrophobic parstatin (1-26) fragment protects the heart by a mechanism involving soluble guanylyl cyclase (sGC), rats were treated with ODQ (1 mg/kg, a sGC inhibitor) with or without the hydrophobic parstatin (1-26) fragment (1 µg/kg) prior to ischemia. As shown in FIG. 8A, ODQ abolished the reduction in infarct size caused by the hydrophobic parstatin (1-26) fragment, but had no effect alone. Tissue accumulation of cGMP was measured after 120 min reperfusion from ischemic and non-ischemic myocardium. In these experiments, the cGMP was measured in the rat hearts by specific ELISA kits according to the manufacturer's instructions (Cayman Chemical, Ann Arbor, Mich.). The hearts (n=6/group) were excised after 120 min reperfusion and immediately frozen in liquid nitrogen, then stored at −80° C. until assayed. Frozen myocardial tissue samples in liquid nitrogen were ground to a fine powder in a stainless-steel mortar. Frozen tissue was dropped into 5-10 volumes (ml of solution/gram of tissue) of 5% trichloroacetic acid (TCA) in water. The samples were homogenized on ice (0-40° C.) using a polytron-type homogenizer. Centrifugation was at 30,000 r.p.m. at room temperature and the supernatant was collected for quantitative immunoassay of cGMP.

As shown in FIG. 8B, an increase of 2.4 and 2.7-fold in cGMP content was observed in the ischemic and non-ischemic myocardium from control rats when compared to sham. Moreover, a 4.6 and 10.9-fold tissue accumulation of cGMP was observed after 120 min reperfusion in the ischemic tissue from the hydrophobic parstatin (1-26) fragment treatment group when compared to the control and sham treated groups respectively (FIG. 8B). No difference in cGMP tissue content was observed between the ischemic and non-ischemic zones within the control groups, however, hydrophobic parstatin (1-26) fragment treatment increased cGMP production in the ischemic zone 2.2-fold.

Figure 9:
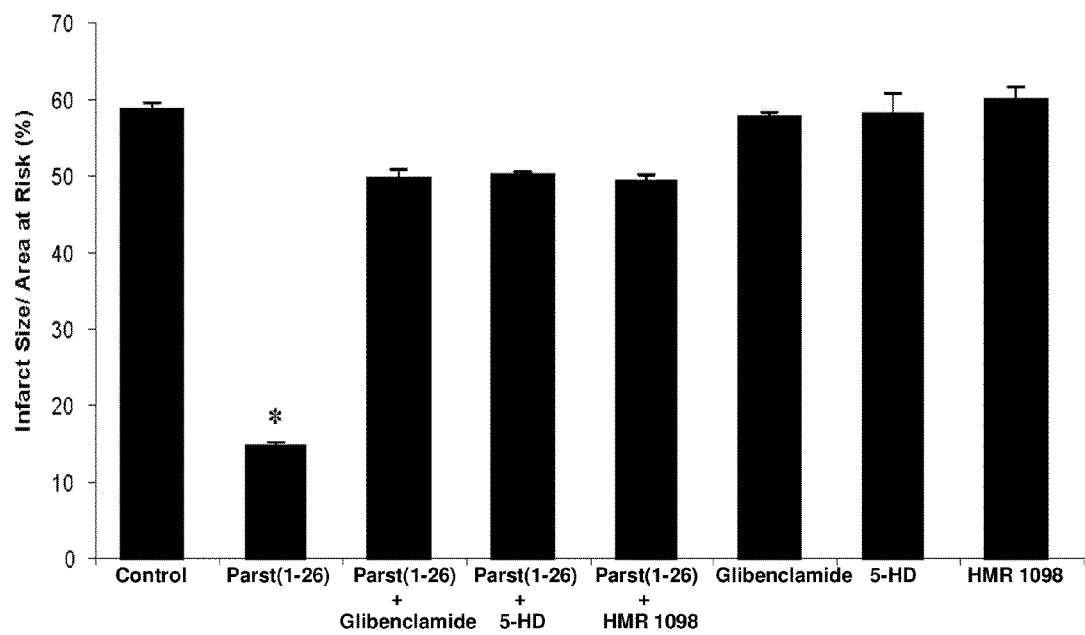
FIG. 9. The cardioprotective effects of hydrophobic parstatin fragment 1-26 are dependent on KATP channels Inhibition of KATP abolished the cardioprotective effects of hydrophobic parstatin fragment 1-26 [parstatin (1-26)]. Glibenclamide (3 mg/kg), HMR 1098 (3 mg/kg) or 5-HD (10 mg/kg) were injected 30 min prior to ischemia. The rats were treated with hydrophobic parstatin fragment 1-26 (1 µg/kg) 15 min prior to ischemia and then subjected to 30 min ischemia and 120 min reperfusion. Control rats received vehicle only. Infarct size is expressed as percentage of area at risk. Data are means±SE, n=6 rats/group, *P<0.01.

To investigate a role for $K^+$ATP channels in mediating hydrophobic parstatin (1-26) fragment-induced cardioprotection, groups were treated with the nonselective $K^+$ATP channel blocker, glibenclamide, alone or with the hydrophobic parstatin fragment 1-26 prior to ischemia. As shown in FIG. 9, glibenclamide (3 mg/kg) completely diminished the cardioprotective effect of hydrophobic parstatin fragment 1-26. Glibenclamide alone had no effect on infarct size. Similarly, HMR 1098 (6 mg/kg, a sarcolemmal KATP channel inhibitor) and 5-HD (10 mg/Kg, a mitochondrial KATP channel antagonist) blocked the cardioprotective effects of hydrophobic parstatin fragment 1-26 (FIG. 9).

Those skilled in the art will recognize, or be able to ascertain using no more than routine experimentation, many equivalents to the specific embodiments of the invention described herein. Such equivalents are intended to be encompassed by the following claims.

All references, patents, and patent publications cited herein are incorporated herein by reference as if they were each incorporated individually.

The invention claimed is:

1. An isolated parstatin peptide 26 amino acids in length, wherein the isolated peptide is at least 95% identical to amino acids 1-26 of SEQ ID NO: 1, and has cardioprotective activity.

2. A pharmaceutical composition comprising the isolated parstatin peptide of claim 1.

3. A method of treatment of aberrant ocular angiogenesis in a subject comprising administration of the isolated parstatin peptide of claim 1.

4. The method of claim 3, further comprising monitoring the subject for treatment of aberrant ocular angiogenesis.

5. The method of claim 3, wherein administration of an isolated parstatin peptide comprises contacting an eye of the subject with of an isolated parstatin peptide.

6. A method of prevention or treatment of myocardial ischemic injury in a subject comprising administration of the isolated parstatin peptide of claim 1.

7. The method of claim 6, wherein myocardial ischemic injury comprises ischemic injury related to surgery.

8. The method of claim 6, wherein myocardial ischemic injury comprises ischemia-reperfusion injury.

9. The method of claim 6, further comprising monitoring the subject for treatment of myocardial ischemic injury.

10. The method of claim 6, wherein administration of an isolated parstatin peptide comprises contacting a heart of the subject with the isolated parstatin peptide.

11. The method of claim 3, wherein the dose of the isolated parstatin peptide ranges from 0.01 to 10 µg/Kg.

12. The method of claim 6, wherein the dose of the isolated parstatin peptide ranges from 0.01 to 10 µg/Kg.

13. The method of claim 6, wherein the dose of the isolated parstatin peptide is 10 µg/Kg.

14. The method of claim 3, wherein the isolated parstatin peptide consists of amino acids 1-26 of SEQ ID NO: 1.

15. The method of claim 6, wherein the isolated parstatin peptide consists of amino acids 1-26 of SEQ ID NO: 1.

16. An isolated parstatin peptide consisting of amino acids 1-26 of SEQ ID NO: 1.

* * * * *